(12) United States Patent
Betsugi

(10) Patent No.: US 11,957,523 B2
(45) Date of Patent: Apr. 16, 2024

(54) SURGICAL INSTRUMENT

(71) Applicant: MEDICAROID CORPORATION, Kobe (JP)

(72) Inventor: Shota Betsugi, Kobe (JP)

(73) Assignee: MEDICAROID CORPORATION, Kobe (JP)

( * ) Notice: Subject to any disclaimer, the term of this patent is extended or adjusted under 35 U.S.C. 154(b) by 137 days.

(21) Appl. No.: 17/330,453

(22) Filed: May 26, 2021

(65) Prior Publication Data
US 2021/0369400 A1    Dec. 2, 2021

(30) Foreign Application Priority Data

May 29, 2020    (JP) .................................. 2020-094073
May 29, 2020    (JP) .................................. 2020-094131

(51) Int. Cl.
*A61B 90/70*    (2016.01)
*B08B 9/032*    (2006.01)
*A61B 34/37*    (2016.01)

(52) U.S. Cl.
CPC .............. *A61B 90/70* (2016.02); *B08B 9/032* (2013.01); *A61B 34/37* (2016.02); *B08B 2209/032* (2013.01)

(58) Field of Classification Search
CPC ... A61B 90/70; A61B 34/37; B08B 2209/032; B08B 9/032
See application file for complete search history.

(56) References Cited

U.S. PATENT DOCUMENTS

| | | | | |
|---|---|---|---|---|
| 4,141,576 A | * | 2/1979 | Lupke | B29C 66/1122 285/903 |
| 4,530,356 A | * | 7/1985 | Helfgott | A61F 9/00763 606/171 |
| 8,398,634 B2 | | 3/2013 | Manzo et al. | |
| 8,795,324 B2 | | 8/2014 | Kawai et al. | |
| 2009/0119856 A1 | * | 5/2009 | Onishi | A61B 1/125 15/104.066 |
| 2014/0305472 A1 | * | 10/2014 | Kawai | A61B 17/2909 134/21 |
| 2018/0360418 A1 | * | 12/2018 | Saul | A61B 8/445 |
| 2021/0219832 A1 | * | 7/2021 | Retailleau | A61B 34/70 |

FOREIGN PATENT DOCUMENTS

| | | | | |
|---|---|---|---|---|
| JP | 2009-028425 A | | 2/2009 | |
| WO | WO-2015138658 A2 | * | 9/2015 | ............. A61B 90/70 |

* cited by examiner

*Primary Examiner* — Joseph L. Perrin
*Assistant Examiner* — Irina Graf
(74) *Attorney, Agent, or Firm* — METROLEX IP LAW GROUP, PLLC

(57) ABSTRACT

A surgical instrument according to an embodiment may include: a shaft; an end effector provided on a side of one end of the shaft; a housing provided on a side of the other end of the shaft and including a base including an attachment surface to be attached to a robot arm, a lid portion covering the base, and cleaning liquid supply holes to supply a cleaning liquid; and a cleaning tube to supply the cleaning liquid into the shaft. The cleaning liquid supply holes include: a first cleaning liquid supply hole to which the cleaning tube is attached; a second cleaning liquid supply hole communicating with an inside of the housing; and a third cleaning liquid supply hole opening in a direction substantially orthogonal to an opening direction of the second cleaning liquid supply hole and communicating with the inside of the housing.

20 Claims, 13 Drawing Sheets

CROSS SECTION ALONG LINE 101-101

CROSS SECTION ALONG LINE 102-102

METHOD OF ASSEMBLING SURGICAL INSTRUMENT

SURGICAL INSTRUMENT

CROSS REFERENCE TO RELATED APPLICATIONS

This application claims priority to Japanese Patent Application No. 2020-94073 filed on May 29, 2020 and Japanese Patent Application No. 2020-94131 filed on May 29, 2020, the entire contents of each of which are incorporated herein by reference.

BACKGROUND

The disclosure may relate to a surgical instrument and may especially relate to a surgical instrument including a cleaning tube.

In a related art, there has been known a surgical instrument including a cleaning tube.

U.S. Pat. No. 8,398,634 discloses a surgical instrument that includes a flush tube (cleaning tube) to flow fluid for introduction of gas during surgery, post-surgery irrigation, and sterilization. In the surgical instrument, the flush tube is introduced in a shaft of the surgical instrument.

SUMMARY

In the surgical instrument disclosed in U.S. Pat. No. 8,398,634, the flush tube is introduced in the shaft so that the inside of the shaft can be cleaned; however, it may be difficult to reliably clean the inside of a housing of the surgical instrument.

An object of an embodiment of the disclosure may be to provide a surgical instrument that is capable of reliably cleaning an inside of a housing of a surgical instrument.

A surgical instrument according to an aspect may include: a shaft; an end effector provided on a side of one end of the shaft; a housing provided on a side of the other end of the shaft and including a base including an attachment surface to be attached to a robot arm, a lid portion covering the base, and cleaning liquid supply holes to supply a cleaning liquid; and a cleaning tube to supply the cleaning liquid into the shaft. The cleaning liquid supply holes include: a first cleaning liquid supply hole to which the cleaning tube is attached; a second cleaning liquid supply hole communicating with an inside of the housing; and a third cleaning liquid supply hole opening in a direction substantially orthogonal to an opening direction of the second cleaning liquid supply hole and communicating with the inside of the housing.

As described above, the surgical instrument according to the aspect may include: the second cleaning liquid supply hole communicating with the inside of the housing; and the third cleaning liquid supply hole opening in the direction substantially orthogonal to the opening direction of the second cleaning liquid supply hole and communicating with the inside of the housing. With this configuration, the cleaning liquid can be supplied into the housing from the second and third cleaning liquid supply holes. As a result, the inside of the housing can be cleaned. Further, the cleaning liquid can be supplied into the housing from the second and third cleaning liquid supply holes along the directions substantially orthogonal to each other, unlike a case where only one of the second and third cleaning liquid supply holes is provided. As a result, it is possible to suppress occurrence of unwashed residue inside the housing more effectively, compared with a case where the cleaning liquid is supplied only in one direction. Therefore, it is possible to provide a surgical instrument that is capable of reliably cleaning an inside of a housing of the surgical instrument.

DETAILED DESCRIPTION

Figure 1:
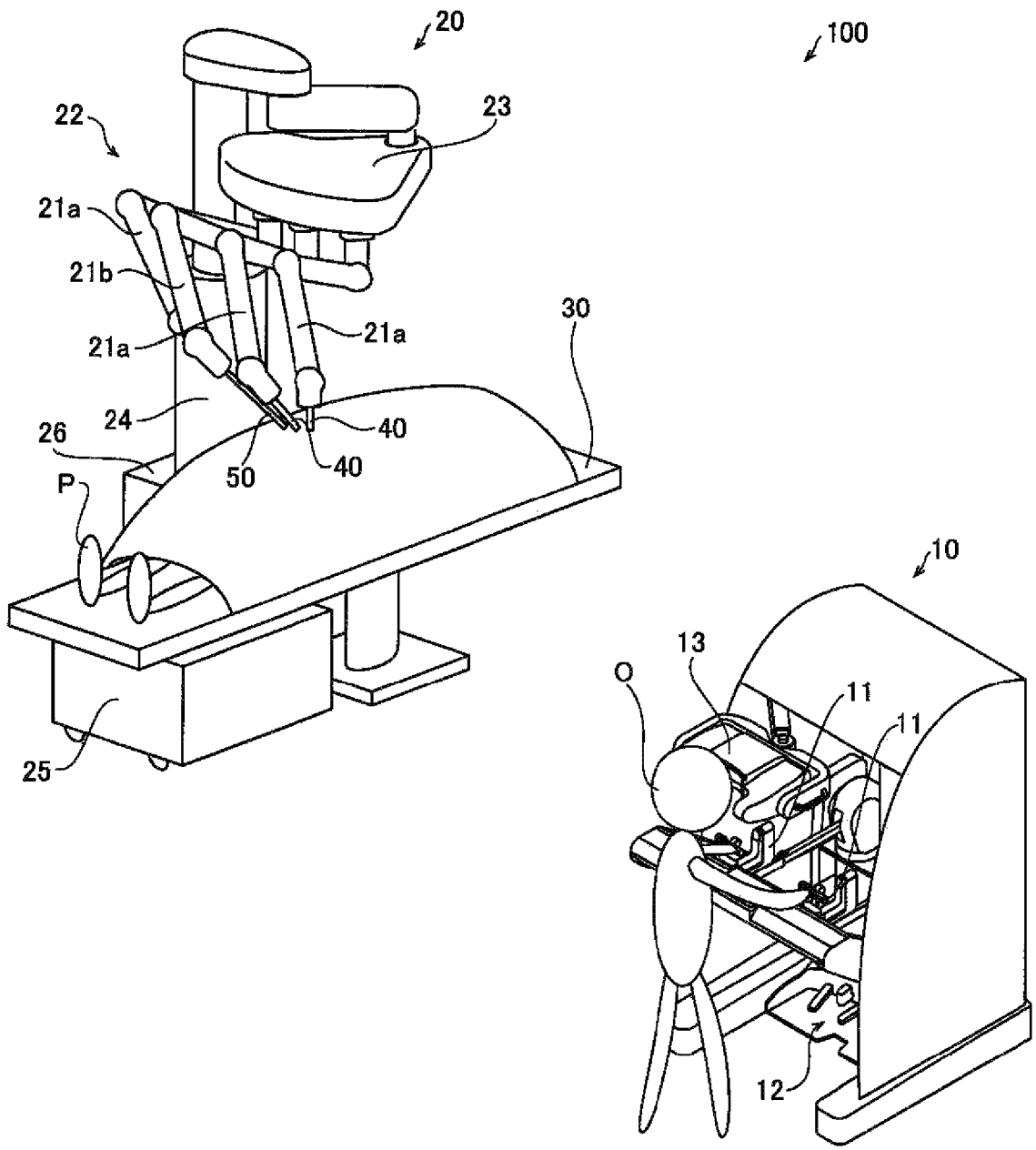
FIG. 1 is a diagram illustrating an overview of a robotic surgical system according to one or more embodiments.

Descriptions are provided hereinbelow for one or more embodiments based on the drawings. In the respective drawings referenced herein, the same constituents are designated by the same reference numerals and duplicate explanation concerning the same constituents is omitted. All of the drawings are provided to illustrate the respective examples only.

First Embodiment (Configuration of Robotic Surgical System)

A configuration of a robotic surgical system 100 according to one or more embodiments is described with reference to FIGS. 1 and 2.

As illustrated in FIG. 1, the robotic surgical system 100 includes a remote control apparatus 10 and a patient-side apparatus 20.

The remote control apparatus 10 is provided to remotely control medical equipment provided to the patient-side apparatus 20. When an operator O, as a surgeon, inputs an action mode instruction to be executed by the patient-side apparatus 20, to the remote control apparatus 10, the remote control apparatus 10 transmits the action mode instruction to the patient-side apparatus 20 through a controller 26. In response to the action mode instruction transmitted from the remote control apparatus 10, the patient-side apparatus 20 operates the medical equipment, such as surgical instruments 40, an endoscope 50, and the like, attached to robot arms 21a and 21b. This allows minimally invasive surgery.

The patient-side apparatus 20 constitutes an interface to perform a surgery for a patient P. The patient-side apparatus 20 is positioned beside an operation table 30 on which the patient P is laid. The patient-side apparatus 20 includes plural robot arms 21a and 21b. One (21b) of the robot arms holds the endoscope 50 and the other robot arms 21a hold the surgical instruments 40. The robot arms 21a and 21b are commonly supported by a platform 23. Each of the robot arms 21a and 21b includes plural joints. Each joint includes a driver (a driving part) provided with a servo-motor and a position detector such as an encoder. The robot arms 21a and 21b are configured so that the medical equipment attached to each of the robot arms 21a and 21b is controlled by a driving signal given through the controller 26 and performs a desired movement.

The platform 23 is supported by a positioner 22 placed on the floor of an operation room. The positioner 22 includes a column 24 and a base 25. The column 24 includes an elevating shaft adjustable in the vertical direction. The base 25 includes wheels and is movable on the floor surface.

Figure 3:
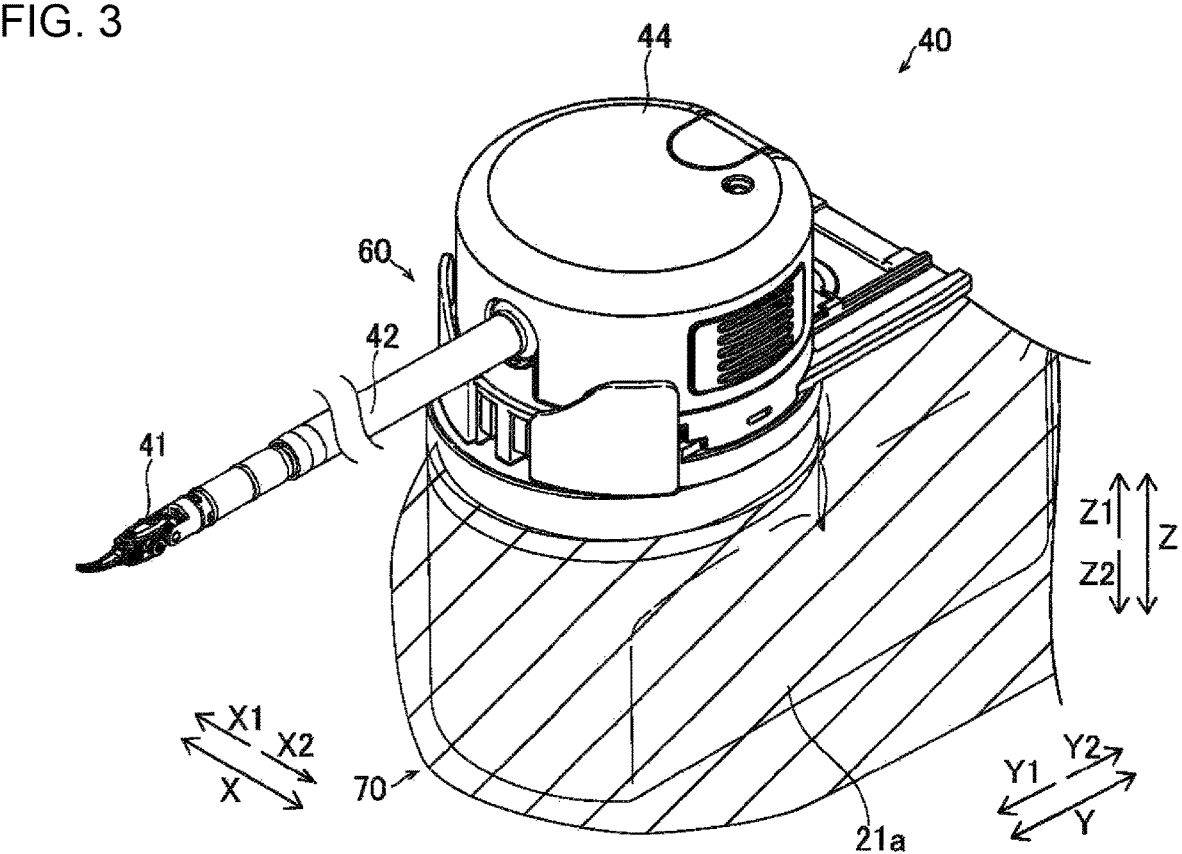
FIG. 3 is a diagram illustrating a perspective view of a state where a surgical instrument is attached to a robot arm via an adaptor according to a first embodiment.

The surgical instruments 40 as the medical equipment are detachably attached to the distal ends of the robot arms 21a. Each of the surgical instrument 40 is detachably connected to the corresponding robot arm 21a of the robotic surgical system 100 through an adaptor 60, as illustrated in FIG. 3.

The surgical instrument 40 includes an end effector 41, and an elongate shaft 42, wherein the end effector 41 is provided on a side of one end (Y1 side) of the shaft 42. The end effector 41 is grasping forceps, scissors, a hook, a high-frequency knife, a snare wire, a clamp, or a stapler, for example. The end effector 41 is not limited to those and can be various types of treatment tools. In surgeries using the patient-side apparatus 20, the robot arms 21a introduce the surgical instruments 40 into the body of the patient P through a cannula (trocar) placed on the body surface of the patient P. The end effectors 41 of the surgical instruments 40 are then located near the surgery site.

To the distal end of the robot arm 21b, the endoscope 50 as the medical equipment is detachably attached. The endoscope 50 captures an image in a body cavity of the patient P. The captured image is outputted to the remote control apparatus 10. The endoscope 50 is a 3D endoscope capable of capturing a three-dimensional image or a 2D endoscope. In surgeries using the patient-side apparatus 20, the robot arm 21b introduces the endoscope 50 into the body of the patient P through a trocar placed on the body surface of the patient P. The endoscope 50 is then located near the surgery site.

The remote control apparatus 10 constitutes the interface with the operator O. The remote control apparatus 10 is an apparatus that allows the operator O to operate the medical equipment attached to the robot arms 21a and 21b. Specifically, the remote control apparatus 10 is configured to transmit action mode instructions which are inputted by the operator O and are to be executed by the surgical instruments 40 and endoscope 50, to the patient-side apparatus 20 through the controller 26. The remote control apparatus 10 is installed beside the operation table 30 so that the operator O can see the condition of the patient P very well while operating the remote control apparatus 10, for example. The remote control apparatus 10 may be configured to transmit action mode instructions wirelessly and installed in a room different from the operation room where the operation table 30 is installed.

The action modes to be executed by the surgical instruments 40 include modes of actions to be taken by each surgical instrument 40 (a series of positions and postures) and actions to be executed by the function of each surgical instrument 40. When the surgical instrument 40 is a pair of grasping forceps, for example, the action modes to be executed by the surgical instrument 40 include roll and pitch positions of the wrist of the end effector 41 and actions to open and close the jaws. When the surgical instrument 40 is a high-frequency knife, the action modes to be executed by the surgical instrument 40 include vibration of the high-frequency knife, specifically, supply of current to the high-frequency knife. When the surgical instrument 40 is a snare wire, the action modes to be executed by the surgical instrument 40 include a capturing action and an action to release the captured object. Further, the action modes may include an action to supply current to a bipolar or monopolar instrument to burn off the surgery site.

The action modes to be executed by the endoscope 50 include the position and posture of the tip of the endoscope 50 and setting of the zoom magnification, for example.

Figure 2:
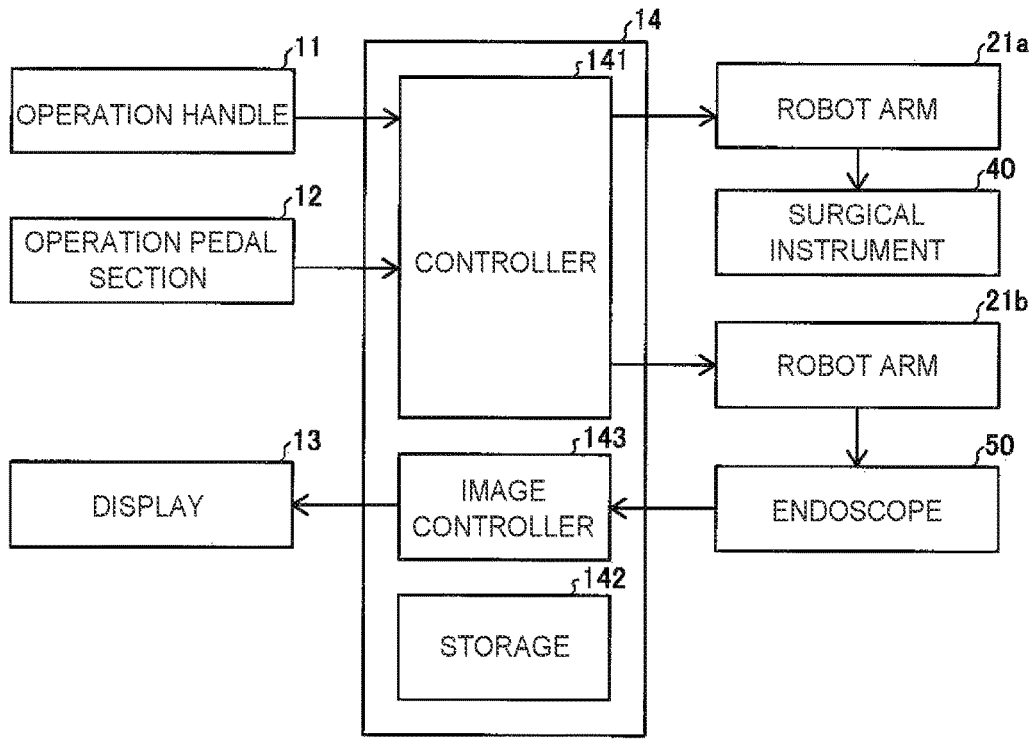
FIG. 2 is a block diagram illustrating a view of a control-related configuration of the robotic surgical system according to one or more embodiments.

As illustrated in FIGS. 1 and 2, the remote control apparatus 10 includes operation handles 11, an operation pedal section 12, a display 13, and a control apparatus 14.

The operation handles 11 are provided in order to remotely operate the medical equipment attached to the robot arms 21a and 21b. Specifically, the operation handles 11 accept operations by the operator O for operating the medical equipment (the surgical instruments 40 and endoscope 50). The operation handles 11 include two operation handles 11 arranged side by side in the horizontal direction. One of the two operation handles 11 is operated by the right hand of the operator O while the other operation handle 11 is operated by the left hand of the operator O.

The operation handles 11 extend from the rear side of the remote control apparatus 10 toward the front side. The operation handles 11 are configured to move in a predetermined three-dimensional operation region. Specifically, the operation handles 11 are configured so as to move up and down, right and left, and forward and rearward.

The remote control apparatus 10 and patient-side apparatus 20 constitute a master-slave system in terms of controlling movement of the robot arms 21a and robot arm 21b. The operation handles 11 constitute an operating part on the master side in the master-slave system, and the robot arms 21a and 21b holding the medical equipment constitute an operating part on the slave side. When the operator O operates the operation handles 11, the movement of one of the robot arms 21a or 21b is controlled so that the distal end portion (the end effector 41 of the surgical instrument 40) of the robot arm 21a or the distal end portion (the endoscope 50) of the robot arm 21b moves following the movement of the operation handles 11.

The patient-side apparatus 20 controls the movement of the robot arms 21a in accordance with the set motion scaling ratio. When the motion scaling ratio is set to ½, for example, the end effectors 41 of the surgical instruments 40 move ½ of the movement distance of the operation handles 11. This allows for precise fine surgery.

The operation pedal section 12 or an operation pedal unit includes plural pedals to execute medical equipment-related functions. The plural pedals include a coagulation pedal, a cutting pedal, a camera pedal, and a clutch pedal. The plural pedals are operated by a foot of the operator O.

The coagulation pedal enables the surgical instrument 40 to coagulate a surgery site. Specifically, when the coagulation pedal is operated, voltage for coagulation is applied to the surgical instrument 40 to coagulate the surgery site. The cutting pedal enables the surgical instrument 40 to cut the surgery site. Specifically, the cutting pedal is operated to apply voltage for cutting to the surgical instrument 40 and cut a surgery site.

The camera pedal is used to control the position and orientation of the endoscope 50 that captures images within the body cavity. Specifically, the camera pedal enables operation of the endoscope 50 by the operation handles 11. That is, the position and orientation of the endoscope 50 are controllable by the operation handles 11 while the camera pedal is being pressed. The endoscope 50 is controlled by using both of the right and left operation handles 11, for example. Specifically, when the operator O rotates the right and left operation handles 11 about the middle point between the right and left operation handles 11, the endoscope 50 is rotated. When the operator O presses the right and left operation handles 11 together, the endoscope 50 goes forward into the body cavity. When the operator O pulls the right and left operation handles 11 together, the endoscope 50 goes back. When the operator O moves the right and left operation handles 11 together up, down, right, or left, the endoscope 50 moves up, down, right, or left, respectively.

The clutch pedal is used to temporarily disconnect operation-related connection between the operation handles 11 and the robot arms 21a to stop movement of the surgical instruments 40. Specifically, when the clutch pedal is being pressed, the robot arms 21a of the patient-side apparatus 20 do not work even if the operation handles 11 are operated. For example, when the operation handles 11 are operated and moved to the edge of the range of movement, the operator O operates the clutch pedal to temporarily disconnect the operation-related connection and then returns the operation handles 11 to the center of the range of movement. When the operator O stops operating the clutch pedal, the operation handles 11 are again connected to the robot arms 21a. The operator O restarts the operation for the operation handles 11 around the center thereof.

The display 13 or a display unit is configured to display images captured by the endoscope 50. The display 13 includes a scope type display or a non-scope type display. The scope type display is a display that the operator O looks into. The non-scope type display is a display like an open-type display that includes a flat screen and the operator O is able to see without looking into, such as normal displays for personal computers.

When the scope type display is attached, the scope type display displays 3D images captured by the endoscope 50 attached to the robot arm 21b of the patient-side apparatus 20. When the non-scope type display is attached, the non-scope type display also displays 3D images captured by the endoscope 50 provided for the patient-side apparatus 20. The non-scope type display may display 2D images captured by the endoscope 50 provided for the patient-side apparatus 20.

As illustrated in FIG. 2, the control apparatus 14 includes a controller 141, a storage 142, and an image controller 143, for example. The controller 141 includes a calculator such as a CPU. The storage 142 includes a memory, such as a ROM and a RAM. The control apparatus 14 may be composed of a single controller performing centralized control or may be composed of plural controllers that perform decentralized control in cooperation with each other. The controller 141 determines whether an action mode instruction inputted by the operation handles 11 is to be executed by the robot arms 21a or to be executed by the endoscope 50, depending on the state of the operation pedal section 12. When determining that the action mode instruction inputted by the operation handles 11 is to be executed by any one of the surgical instruments 40, the controller 141 transmits the action mode instruction to the corresponding robot arm 21a. The robot arm 21a is thereby driven for controlling movement of the surgical instrument 40 attached to the robot arm 21a.

When determining that the action mode instruction inputted by the operation handles 11 is to be executed by the endoscope 50, the controller 141 transmits the action mode instruction to the robot arm 21b. The robot arm 21b is thereby driven for control of movement of the endoscope 50 attached to the robot arm 21b.

The storage 142 stores control programs corresponding to the types of the surgical instrument 40, for example. The controller 141 reads the stored control programs according to the types of the attached surgical instruments 40. The action mode instructions from the operation handles 11 and/or the operation pedal section 12 of the remote control apparatus 10 thereby cause the respective surgical instruments 40 to perform proper movements.

The image controller 143 transmits images acquired by the endoscope 50 to the display 13. The image controller 143 performs processing and modifying the images when needed.

(Configurations of Adaptor and Surgical Instrument)

With reference to FIGS. 3 to 7, a configuration of the surgical instrument 40 according to a first embodiment is described.

As illustrated in FIG. 3, the surgical instrument 40 is a surgical instrument that is detachably attached to the robot arm 21a of the robotic surgical system 100. The robot arm 21a is used in a clean area and is covered with the drape 70. In operation rooms, clean technique is used in order to prevent surgical incision sites and medical equipment from being contaminated by pathogen, foreign matters, or the like. The clean technique defines a clean area and a contaminated area, which is outside the clean area. The surgery sites are located in the clean area. Members of the surgical team, including the operator O, make sure that only sterile objects are placed in the clean area during surgery and perform sterilization for an object which is to be moved to the clean area from the contaminated area. Similarly, when the members of the surgical team including the operator O place their hands in the contaminated area, the members sterilize their hands before directly touching objects located in the clean area. Instruments used in the clean area are sterilized or are covered with sterile drape 70.

The drape 70 is arranged between the robot arm 21a and the surgical instrument 40. Specifically, the drape 70 is arranged between the adaptor 60 and the robot arm 21a. Further, the drape 70 is arranged between the robot arm 21b and the endoscope 50. The adaptor 60 is attached to the robot arm 21a while putting the drape 70 between the adaptor 60 and the robot arm 21a. Specifically, the adaptor 60 is a drape adaptor that puts the drape 70 between the adaptor 60 and the robot arm 21a. The drape 70 is thus able to be mounted through the adaptor 60. The surgical instrument 40 is attached to the adaptor 60 that is attached to the robot arm 21a with the drape 70 interposed therebetween. The robot arm 21a transmits driving force to the surgical instrument 40 through the adaptor 60 to drive the end effector 41 of the surgical instrument 40.

Figure 4:
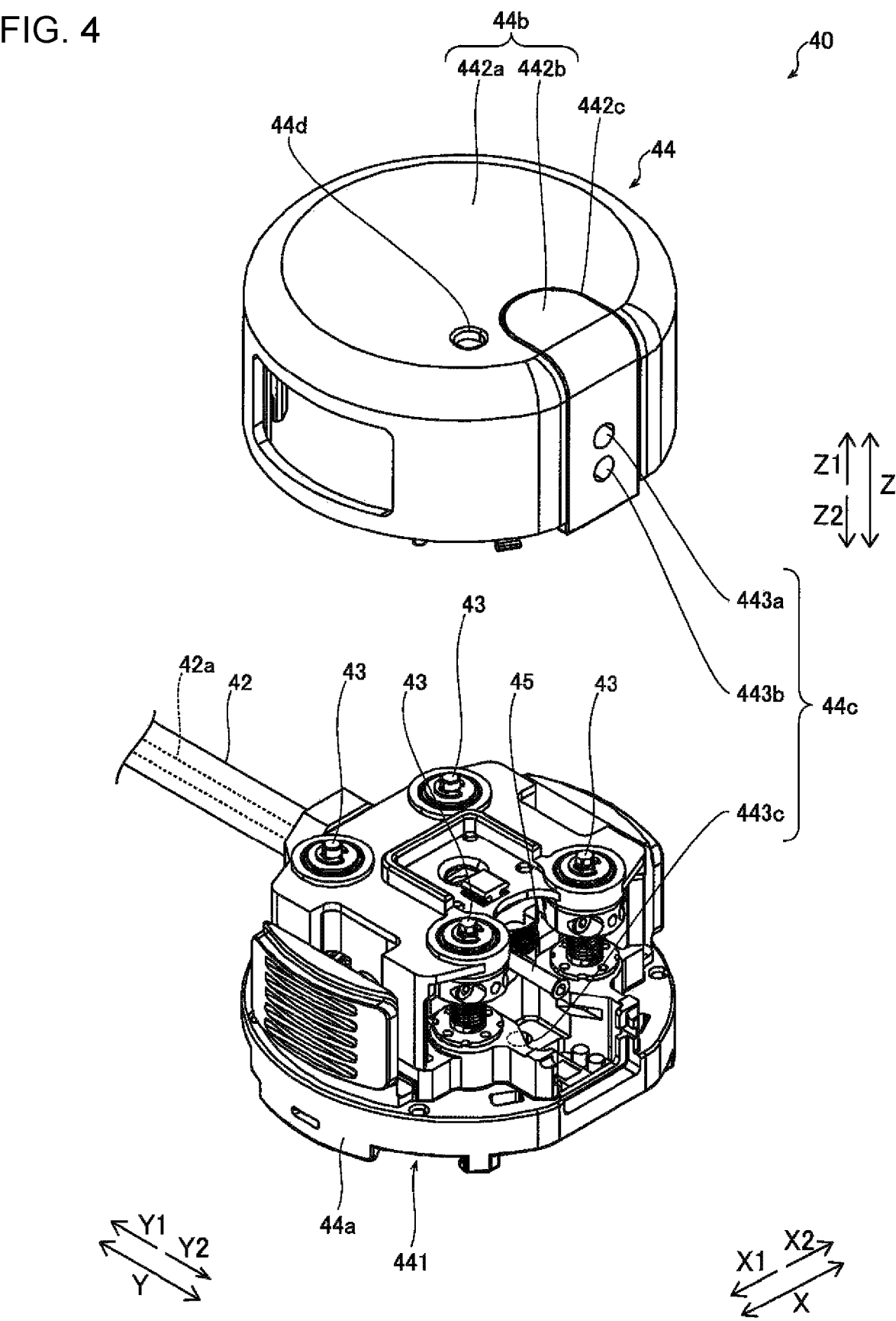
FIG. 4 is a diagram illustrating a perspective view of a state where a lid portion is detached from a base according to a first embodiment.

As illustrated FIG. 4, the surgical instrument 40 includes a plurality (four) of driven members 43, a housing 44, and a cleaning tube 45, in addition to the end effector 41 (see FIG. 3) and the shaft 42.

The plural driven members 43 are driven to rotate to drive the end effector 41. The driven members 43 are provided to a base 44a (described later) of the housing 44 and are rotatable about respective rotation axes extending along the Z direction (Z axis direction) with respect to the base 44a of the housing 44. Three of the plural (four) driven members 43 are connected to the end effector 41 with elongate elements 42a passing through the inside of the shaft 42. The elongate elements 42a are, for example, wires, cables, or rods. When being rotated, the three driven members 43 draw the elongate elements 42a to drive the end effector 41. The other one of the plural (four) driven members 43 is connected to the shaft 42 via a shaft drive member 42b (see FIG. 7) such as a gear. When being rotated, the other one driven member 43 rotates the shaft drive member 42b to rotate the shaft 42 about the rotational axis of the shaft 42 extending the Y direction. The four driven members 43 are arranged in two rows in the X direction and two columns in the Y direction. The driven members 43 are provided in the housing 44.

The housing 44 includes the base 44a, a lid portion 44b, and cleaning liquid supply holes 44c. The base 44a is formed with an adaptor attachment surface 441 on a Z2 side of the base 44a. The adaptor attachment surface 441 is an attachment surface at which the surgical instrument 40 is to be attached to the robot arm 21a via the adaptor 60. The driven members 43 are rotatably provided on the base 44a. The base 44a is provided on a side (Y2 side) of the other end of the shaft 42.

The lid portion 44b is configured to cover the base 44a. Specifically, the lid portion 44b is configured to cover the base 44a from a side (Z1 side) opposite from a side of the attachment surface 441 of the base 44a. The lid portion 44b is also configured to detachably attached to the base 44a.

Figure 5:
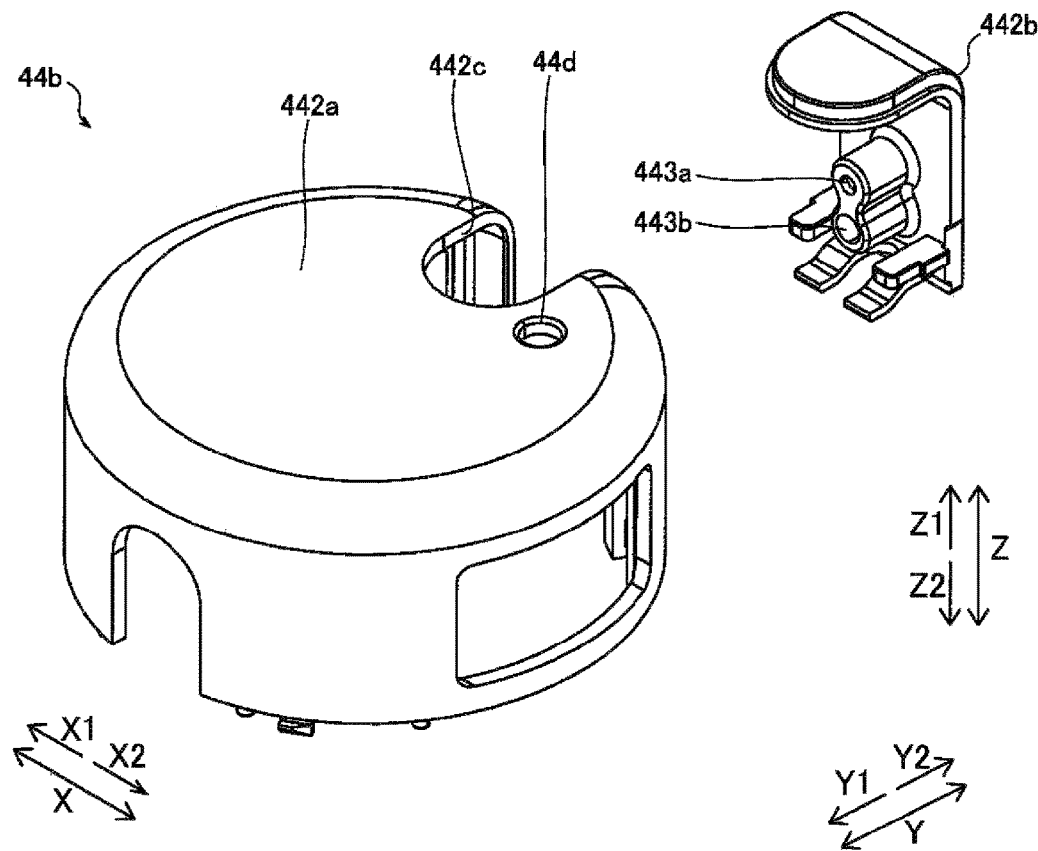
FIG. 5 is a diagram illustrating an exploded perspective view of the lid portion according to a first embodiment.

As illustrated in FIGS. 4 and 5, the lid portion 44b includes a first portion 442a (a first member 442a) and a second portion 442b (a second member 442b) that are separable from each other. The first portion 442a is configured to cover a substantially entirety of the base 44a. The second portion 442b is configured to cover the rest portion of the base 44a that is not covered by the first portion 442a. The first lid portion 442a is formed with a notch 442c (a cutout or a removed portion) for disposing the second lid portion 442b. The notch 442c is provided at a portion of the first lid portion 442a on the Y2 side.

As illustrated in FIG. 4, the cleaning liquid supply holes 44c are provided to supply a cleaning liquid (such as water). In a first embodiment, the cleaning liquid supply holes 44c include: a first cleaning liquid supply hole 443a to which the cleaning tube 45 is attached, a second cleaning liquid supply hole 443b communicating with the inside of the housing 44, and a third cleaning liquid supply hole 443c opening in a direction (Z direction) substantially orthogonal to an opening direction (Y direction) of the second cleaning liquid supply hole 443b and communicating with the inside of the housing 44.

As described above, a first embodiment is provided with: the second cleaning liquid supply hole 443b communicating with the inside of the housing 44; and the third cleaning liquid supply hole 443c opening in the direction substantially orthogonal to the opening direction of the second cleaning liquid supply hole 443b and communicating with the inside of the housing 44. With this configuration, the cleaning liquid can be supplied into the housing 44 from the second and third cleaning liquid supply holes 443b and 443c. As a result, the inside of the housing 44 can be cleaned. Further, in a first embodiment, the cleaning liquid can be supplied into the housing 44 from the second and third cleaning liquid supply holes 443b and 443c along the directions substantially orthogonal to each other, unlike a case where only one of the second and third cleaning liquid supply holes 443b and 443c is provided. As a result, it is possible to effectively suppress the occurrence of unwashed residue inside the housing 44, compared with a case where the cleaning liquid is supplied into the housing 44 only in one direction. Thus, the inside of the housing 44 can be reliably cleaned.

Figure 7:
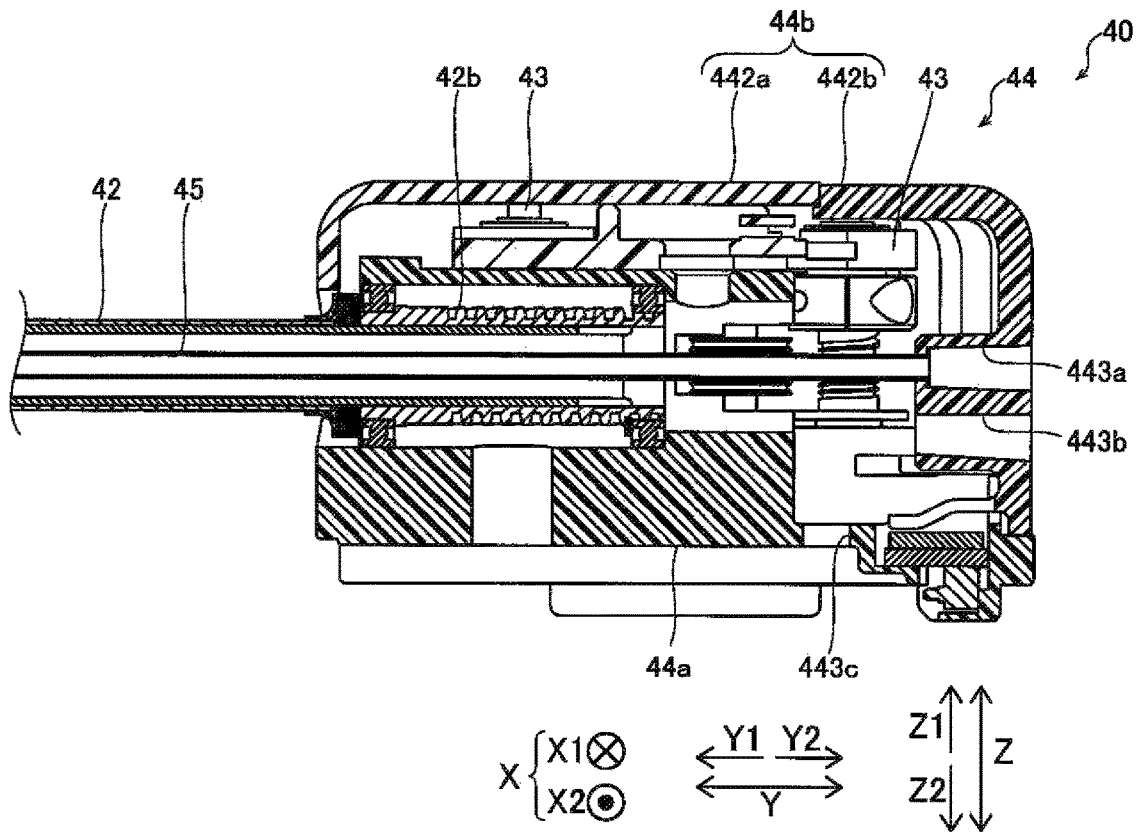
FIG. 7 is a diagram illustrating a cross sectional view of the surgical instrument according to a first embodiment.

As illustrated in FIGS. 4, 5, and 7, the first cleaning liquid supply hole 443a is provided to open in the axial direction (Y direction) of the shaft 42. The first cleaning liquid supply hole 443a is configured to be able to supply the cleaning liquid into the inside of the cleaning tube 45 from the outside of the housing 44. Specifically, the first cleaning liquid supply hole 443a is configured to be able to supply the cleaning liquid into the inside of the cleaning tube 45 along the axial direction (Y direction) of the shaft 42 toward the side (Y1 side) of the one end of the shaft 42. The first cleaning liquid supply hole 443a is configured to be able to supply the cleaning liquid into the inside of the shaft 42 through the cleaning tube 45.

The first cleaning liquid supply hole 443a is provided at the lid portion 44b of the housing 44. Specifically, the first cleaning liquid supply hole 443a is provided at the second portion 442b of the lid portion 44b. The first cleaning liquid supply hole 443a is provided in the second portion 442b of the lid portion 44b so as to open in the axial direction (Y direction) of the shaft 42. The first cleaning liquid supply hole 443a is formed as a through hole penetrating the second portion 442b of the lid portion 44b in the axial direction (Y direction) of the shaft 42.

As illustrated in FIGS. 4, 5, and 7, the second cleaning liquid supply hole 443b is provided to open in the axial direction (Y direction) of the shaft 42. The second cleaning liquid supply hole 443b is configured to supply the cleaning liquid from the outside of the housing 44 into the inside of the housing 44. Specifically, the second cleaning liquid supply hole 443b is configured to be able to supply the cleaning liquid into the inside of the housing 44 along the axial direction (Y direction) of the shaft 42 toward the one end side (Y1 side) of the shaft 42. The second cleaning liquid supply hole 443b is configured to be able to supply the cleaning liquid directly into the inside of the housing 44 from an opening end thereof on a side of the interior of the housing 44, without a cleaning tube attached thereto.

The second cleaning liquid supply hole 443b is provided at the lid portion 44b of the housing 44. Specifically, the second cleaning liquid supply hole 443b is provided at the second portion 442b of the lid portion 44b. The second cleaning liquid supply hole 443b is provided in the second portion 442b of the lid portion 44b so as to open in the axial direction (Y direction) of the shaft 42. The second cleaning liquid supply hole 443b is formed as a through hole penetrating the second portion 442b of the lid portion 44b in the axial direction (Y direction) of the shaft 42. In a first embodiment, the first cleaning liquid supply hole 443a and the second cleaning liquid supply hole 443b are both provided at the lid portion 44b of the housing 44. Specifically, the first cleaning liquid supply hole 443a and the second cleaning liquid supply hole 443b are arranged side by side in the Z direction in the second portion 442b of the lid portion 44b.

Figure 6:
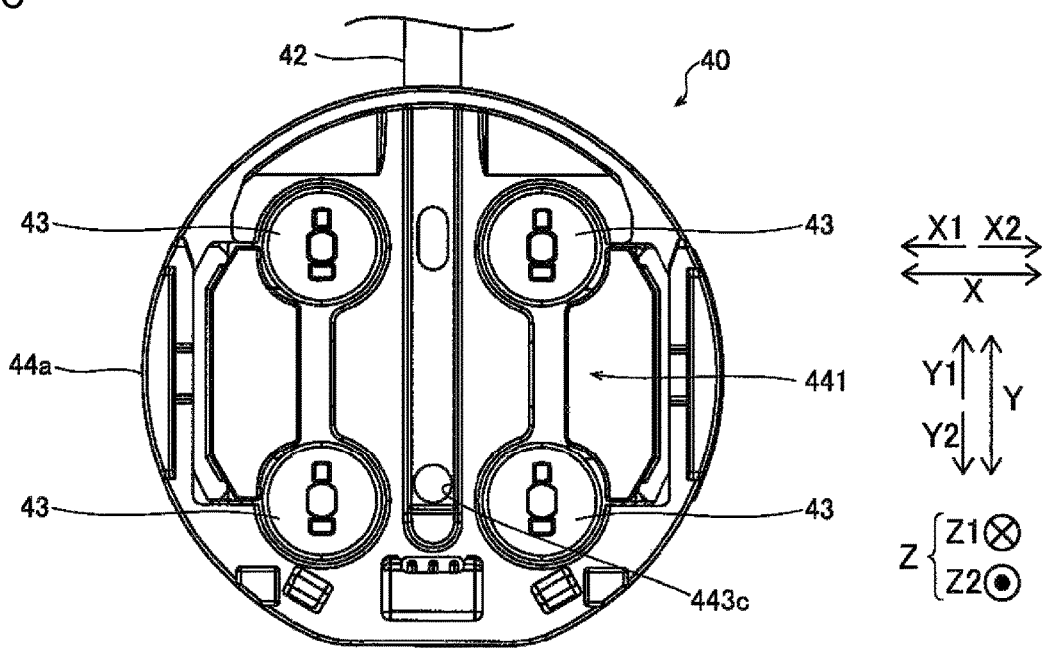
FIG. 6 is a diagram illustrating a view of the surgical instrument according to a first embodiment as seen from the Z2 side.

As illustrated in FIGS. 4, 6, and 7, the third cleaning liquid supply hole 443c is provided to open in the direction (Z direction) substantially orthogonal to the axial direction (Y direction) of the shaft 42. That is, the second cleaning liquid supply hole 443b is provided to open in the axial direction (Y direction) of the shaft 42, and the third cleaning liquid supply hole 443c is provided to open in the direction (Z direction) substantially orthogonal to the axial direction (Y direction) of the shaft 42. With this configuration, the cleaning liquid can be supplied in the axial direction (Y direction) of the shaft 42 through the second cleaning liquid supply hole 443b and can be supplied in the direction (Z direction) substantially orthogonal to the axial direction (Y direction) of the shaft 42 through the third cleaning liquid supply hole 443c. As a result, it is possible to effectively suppress the occurrence of unwashed residue in the housing 44 in both the axial direction (Y direction) of the shaft 42 and the direction (Z direction) substantially orthogonal to the axial direction (Y direction) of the shaft 42.

The third cleaning liquid supply hole 443c is configured to be able to supply the cleaning liquid from the outside of the housing 44 into the inside of the housing 44. Specifically, the third cleaning liquid supply hole 443c is configured to be able to supply the cleaning liquid to the inside of the housing 44 along the direction (Z direction) substantially orthogonal to the axial direction (Y direction) of the shaft 42 toward the inside of the housing 44 (Z1 direction). The third cleaning liquid supply hole 443c is configured to supply the cleaning liquid directly to the inside of the housing 44 from an opening end thereof on a side of the interior of the housing 44, without a cleaning tube attached thereto.

The third cleaning liquid supply hole 443c is provided at the base 44a. Therefore, the third cleaning liquid supply hole 443c can be easily provided, unlike a case where the third cleaning liquid supply hole 443c is provided at the lid portion 44b. Further, unlike the case where the third cleaning liquid supply hole 443c is provided at the lid portion 44b which is easily visible from the outside, it is possible to suppress the deterioration of the aesthetic appearance of the housing 44. Specifically, the third cleaning liquid supply hole 443c is provided to open at the attachment surface 441 of the base 44a in the direction (Z direction) substantially orthogonal to the attachment surface 441 of the base 44a. With this configuration, the cleaning liquid can be supplied in the direction (Z direction) substantially orthogonal to the attachment surface 441 of the base 44a through the third cleaning liquid supply hole 443c. As a result, it is possible to suppress the occurrence of unwashed residue inside the housing 44 with respect to the direction (Z direction) substantially orthogonal to the attachment surface 441 of the base 44a. Further, since the third cleaning liquid supply hole 443c is provided at the attachment surface 441, it is possible to prevent the third cleaning liquid supply hole 443c from being exposed to the outside of the housing 44 in a state where the surgical instrument 40 is attached to the robot arm 21a. With this, in the state where the surgical instrument 40 is attached to the robot arm 21, it is possible to prevent foreign matter from entering the inside of the housing 44 through the third cleaning liquid supply hole 443c. Further, the third cleaning liquid supply hole 443c is formed as a through hole penetrating the base 44a in the direction (Z direction) substantially orthogonal to the axial direction (Y direction) of the shaft 42 and substantially orthogonal to the attachment surface 441.

In a first embodiment, as illustrated in FIG. 6, the third cleaning liquid supply hole 443c is provided at a position off the center of the base 44a. With this configuration, unlike a case where the third cleaning liquid supply hole 443c is provided at the center of the base 44a, it is possible to suppress dispersion of the cleaning liquid supplied from the third cleaning liquid supply hole 443c. That is, it is possible to generate a flow of the cleaning liquid (relatively large flow) from the third cleaning liquid supply hole 443c provided at the position shifted from the center of the base 44a toward the side opposite to the third cleaning liquid supply hole 443c. As a result, unlike the case where the third cleaning liquid supply hole 443c is provided at the center of the base 44a, it is possible to flow the cleaning liquid in a form of a strong current in the housing 44. Thus, the inside of the housing 44 can be cleaned more reliably.

Specifically, the third cleaning liquid supply hole 443c is provided at the position shifted from the center of the base 44a in the axial direction (Y direction) of the shaft 42. With this configuration, it is possible to suppress the dispersion of the cleaning liquid supplied from the third cleaning liquid supply hole 443c in the axial direction of the shaft 42 (Y direction). That is, it is possible to generate the flow of the cleaning liquid from the third cleaning liquid supply hole 443c provided at the position shifted from the center of the base 44a toward the side opposite to the third cleaning liquid supply hole 443c. As a result, it is possible to flow the cleaning liquid in a form of a strong current in the axial direction (Y direction) of the shaft 42. Further, with respect to the direction (X direction) substantially orthogonal to the axial direction (Y direction) of the shaft 42 and substantially parallel to the attachment surface 441 of the base 44a, the third cleaning liquid supply hole 443c is aligned with the center position of the base 44a.

In a first embodiment, as illustrated in FIGS. 6 and 7, the third cleaning liquid supply hole 443c is provided at the position in the base 44a on the side (Y2 side) opposite to the shaft 42. Accordingly, unlike a case where the third cleaning liquid supply hole 443c is provided at a position in the base 44a on the shaft 42 side, the cleaning liquid can be supplied to the inside of the housing 44 from the third cleaning liquid supply hole 443c at the position not interfering the structure for driving the shaft 42 (e.g., the shaft drive member 42b) and the like. As a result, the cleaning liquid can be supplied to the inside of the housing 44 while suppressing the flow of the cleaning liquid from being obstructed by the structure for driving the shaft 42 (e.g., the shaft drive member 42b) or the like. The third cleaning liquid supply hole 443c is shifted from the structure for driving the shaft 42 (e.g., the shaft drive member 42b) in the axial direction (Y direction) of the shaft 42, so as not to face the structure for driving the shaft 42 (e.g., the shaft drive member 42b) in the Z direction.

In a first embodiment, as illustrated in FIG. 7, the first cleaning liquid supply hole 443a, the second cleaning liquid supply hole 443b, and the third cleaning liquid supply hole 443c are provided in the same plane (YZ plane). With this configuration, the worker who performs cleaning can easily recognize the positional relationship between the first cleaning liquid supply hole 443a, the second cleaning liquid supply hole 443b, and the third cleaning liquid supply hole 443c. As a result, the operation of cleaning the surgical instrument 40 by using the first cleaning liquid supply hole 443a, the second cleaning liquid supply hole 443b, and the third cleaning liquid supply hole 443c can be easily performed.

Specifically, the first cleaning liquid supply hole 443a, the second cleaning liquid supply hole 443b, and the third cleaning liquid supply hole 443c are provided in the same plane (YZ plane) passing the axis of the shaft 42. With this configuration, the worker who performs cleaning can more easily recognize the positional relationship between the first cleaning liquid supply hole 443a, the second cleaning liquid supply hole 443b, and the third cleaning liquid supply hole 443c. As a result, the cleaning operation of the surgical instrument 40 by using the first cleaning liquid supply hole 443a, the second cleaning liquid supply hole 443b, and the third cleaning liquid supply hole 443c can be more easily performed.

The first cleaning liquid supply hole 443a and the second cleaning liquid supply hole 443b are provided to open toward the same direction (the axial direction of the shaft 42) in the same plane (YZ plane) passing the axis of the shaft 42. The first and second cleaning liquid supply holes 443a and 443b are provided to open toward the direction different from (substantially orthogonal to) that of the third cleaning liquid supply hole 443c in the same plane (YZ plane) passing the axis of the shaft 42. Further, the first, second, and third cleaning liquid supply holes 443a, 443b, and 443c are aligned with the center position of the surgical instrument 40, with respect to the direction (X direction) substantially orthogonal to the axial direction (Y direction) of the shaft 42 and substantially parallel to the attachment surface 441 of the base 44a.

The first cleaning liquid supply hole 443a, the second cleaning liquid supply hole 443b, and the third cleaning liquid supply hole 443c are provided one by one. With this configuration, the cleaning of the surgical instrument 40 by using the first cleaning liquid supply hole 443a, the second cleaning liquid supply hole 443b, and the third cleaning liquid supply hole 443c can be more easily performed than a case where a plurality of first cleaning liquid supply holes 443a, a plurality of second cleaning liquid supply holes 443b, and a plurality of third cleaning liquid supply holes 443c are provided.

As illustrated in FIGS. 4 and 7, the cleaning tube 45 is provided to supply the cleaning liquid to the inside of the shaft 42. The cleaning tube 45 is attached to the first cleaning liquid supply hole 443a. The cleaning tube 45 is inserted in the shaft 42 in the state where the cleaning tube 45 is attached to the first cleaning liquid supply hole 443a. Although not illustrated, the cleaning tube 45 communicates with the inside of the shaft 42 at the one end side (Y1 side) of the shaft 42.

(Operation of Cleaning Surgical Instrument)

Figure 8:
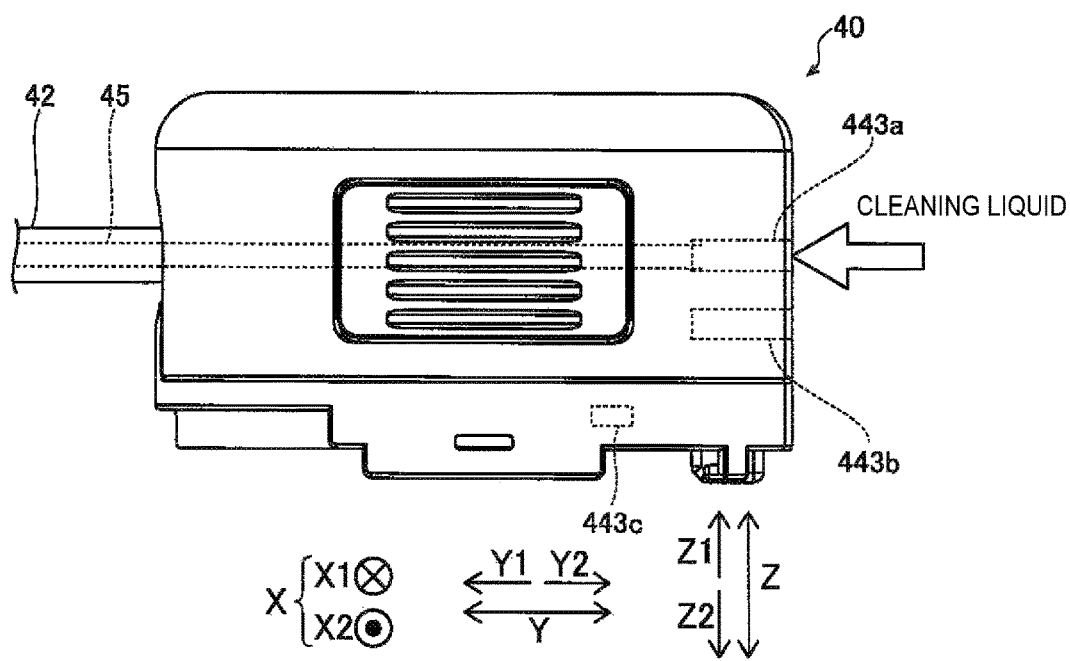
FIG. 8 is a diagram illustrating a first explanatory view for explaining operation of cleaning the surgical instrument according to a first embodiment.
Figure 9:
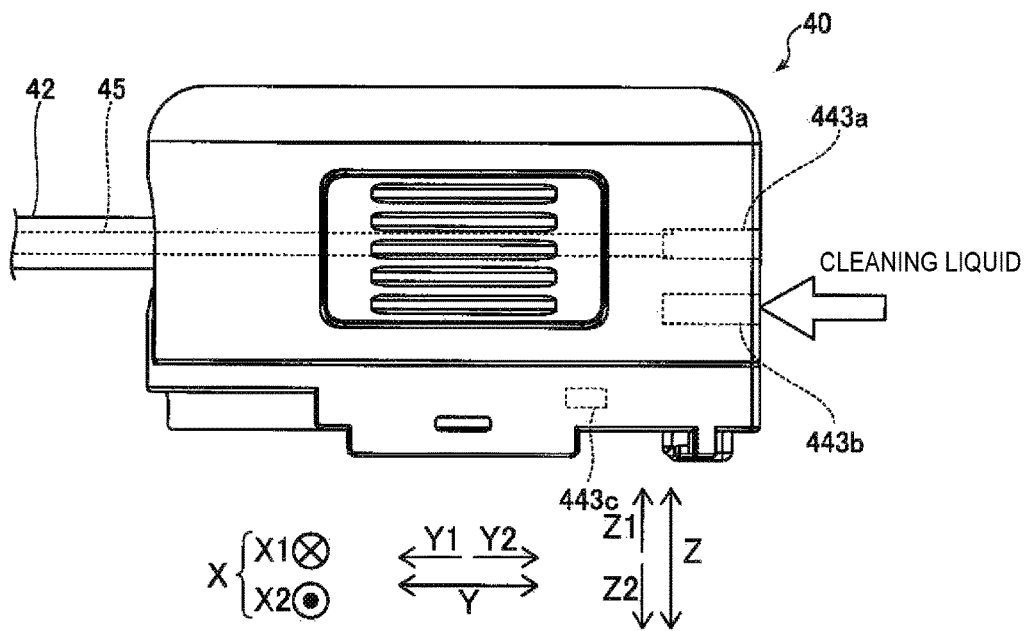
FIG. 9 is a diagram illustrating a second explanatory view for explaining the operation of cleaning the surgical instrument according to a first embodiment.
Figure 10:
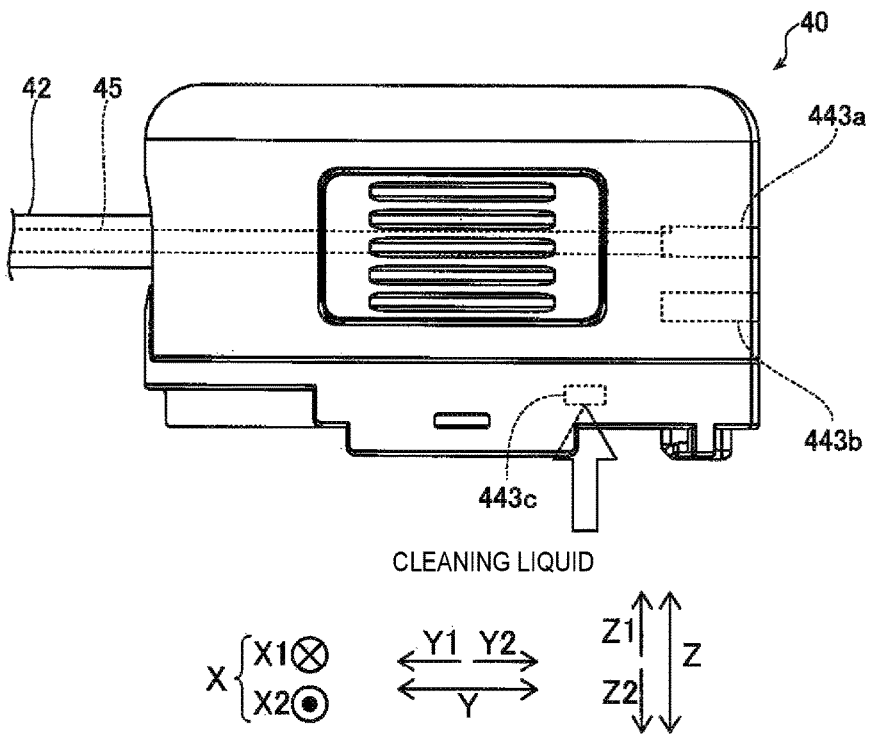
FIG. 10 is a diagram illustrating a third explanatory view for explaining the operation of cleaning the surgical instrument according to a first embodiment.

With reference to FIGS. 8 to 10, operation of cleaning the surgical instrument 40 according to an embodiment is described. The cleaning operation of the surgical instrument 40 is performed at each surgery, for example, in order to clean stains such as blood and pieces generated by the surgery. Here, a case where the worker manually performs the cleaning operation of the surgical instrument 40 is described.

First, as illustrated in FIG. 8, the worker uses a cleaning device such as a syringe filled with cleaning liquid and supplies the cleaning liquid to the inside of the cleaning tube 45 from the first cleaning liquid supply hole 443a. The cleaning liquid supplied into the cleaning tube 45 flows in the cleaning tube 45 in the Y1 direction. The cleaning liquid flowing in the cleaning tube 45 then enters into the shaft 42 at the one end side of the shaft 42. Then, the cleaning liquid entered in the shaft 42 flows in the shaft 42 in the Y2 direction. The cleaning liquid flowing in the shaft 42 cleans the inside of the shaft 42. Then, the cleaning liquid that has cleaned the inside of the shaft flows into the housing 44, and then flows out from the housing 44 though gaps existing in the housing 44.

Next, as illustrated in FIG. 9, the worker uses a cleaning device such as a syringe filled with cleaning liquid and supplies the cleaning liquid to the inside of the housing 44 from the second cleaning liquid supply hole 443b. The supplied cleaning liquid enters into the housing 44 in the Y1 direction from the opening end of the second cleaning liquid supply hole 443b on the inner side of the housing 44. Then, the cleaning liquid that has entered in the housing 44 in the Y1 direction cleans the inside of the housing 44. Then, the cleaning liquid that has cleaned the inside of the housing 44 flows out from the housing 44 though the gaps existing in the housing 44.

Next, as illustrated in FIG. 10, the worker uses a cleaning device such as a syringe filled with cleaning liquid and supplies the cleaning liquid to the inside of the housing 44 from the third cleaning liquid supply hole 443c. The supplied cleaning liquid enters into the housing 44 in the Z1 direction from the opening end of the third cleaning liquid supply hole 443c on the inner side of the housing 44. Then, the cleaning liquid that has entered in the housing 44 from the third cleaning liquid supply hole 443c in the Z1 direction cleans the inside of the housing 44 as a flow of the cleaning liquid which is different from a flow of the cleaning liquid having entered from the second cleaning liquid supply hole 443b. Thus, the inside of the housing 44 can be reliably cleaned. Then, the cleaning liquid that has cleaned the inside of the housing 44 flows out from the housing 44 though the gaps existing in the housing 44.

(Configuration Related to Manual Operation)

With reference to FIGS. 4, 5, and 11 to 13, a configuration related to a manual operation of the surgical instrument 40 according to an embodiment is described.

Figure 11:
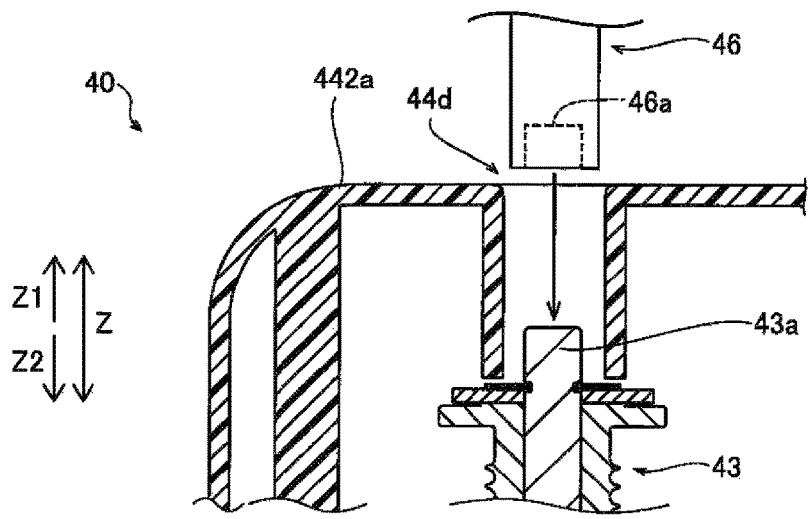
FIG. 11 is a diagram illustrating a cross sectional view of a part in the vicinity of an opening for manual operation of the lid portion of the surgical instrument according to a first embodiment.

As illustrated in FIGS. 4, 5, and 11, the housing 44 includes a manual operation opening 44d (window) for manually manipulating the driven member(s) 43 to operate the end effector 41. The user can insert a manual operation tool 46 in the housing 44 through the manual operation opening 44d and operate the driven member(s) 43 so as to open and close the end effector 41. Specifically, the user can open and close the end effector 41 by engaging an engagement portion 46a (described later) of the manual operation tool 46 with an engagement portion 43a provided at an end of the driven member 43, and then manually rotating the driven member 43 by using the manual operation tool 46. The manual operation opening 44d is provided at the first lid portion 442a of the lid portion 44b.

Figure 12:
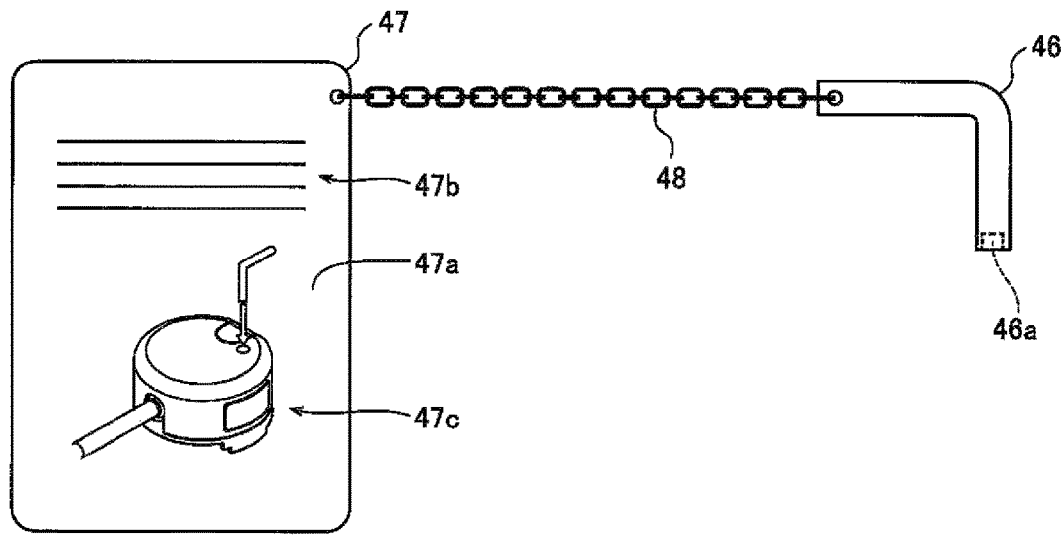
FIG. 12 is a diagram illustrating a view of a tool for manual operation according to an embodiment.

As illustrated in FIG. 12, the manual operation tool 46 is an L-shaped wrench. The manual operation tool 46 includes the engagement portion 46a to be engaged with the engagement portion 43a (see FIG. 11) of the driven member 43. The engagement portion 46a is provided at a distal end portion of the manual operation tool 46. The engagement portion 46a is formed as a concave or recess portion.

To the manual operation tool 46, an explanation plate 47 is connected via a connecting member 48 such as a chain. The explanation plate 47 is made of a sheet metal of aluminum. An explanation description surface 47a of the explanation plate 47 describes how to use the manual operation tool 46. Specifically, the explanation description surface 47a of the explanation plate 47 includes: an explanatory text portion 47b including explanatory text of how to use the manual operation tool 46; and an explanatory diagram portion 47c including an explanatory diagram(s) of how to use the manual operation tool 46.

Here, the explanation plate 47 made of the aluminum sheet metal may be corroded when washed with alkaline detergent. In a case where the explanation plate 47 is corroded, it may be inconvenient that the explanation portion (explanatory text portion 47b and explanatory diagram portion 47c) disappears.

Figure 13:
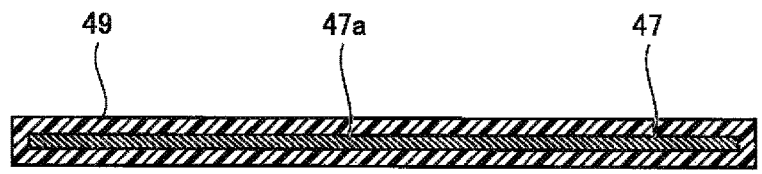
FIG. 13 is a diagram illustrating a view of an explanation plate for the manual operation tool according to an embodiment.

Therefore, in a first embodiment, as illustrated in FIG. 13, the explanation plate 47 is coated with a resin film 49 having corrosion resistance to the alkaline detergent. As a result, it is possible to prevent the explanation plate 47 from being corroded and prevent the explanation portion from disappearing during cleaning with the alkaline detergent. The resin material of the resin film 49 is not particularly limited as long as it has corrosion resistance to the alkaline detergent, but an epoxy resin can be used, for example. The resin film 49 is provided so as to coat the entire explanation plate 47 including the explanation description surface 47a.

Second Embodiment

In such a surgical instrument disclosed in the U.S. Pat. No. 8,398,634, the arrangement of the flashtube may be changed in order to make the housing compact. The inventor(s) of the present application realize(s) a problem may occur, depending on how the flashtube is arranged, in which the flashtube (cleaning tube) would come off the housing (pop out of the housing) during cleaning of the shaft when the cleaning liquid is supplied from the flashtube to the inside of the shaft due to the pressure of the flow of the cleaning liquid that turns back from the distal end toward the proximal end of the shaft. Further, in such a surgical instrument disclosed in the U.S. Pat. No. 8,398,634, when operating the end effector by using the cable passing through the inside of the shaft, the flash tube (cleaning tube) may come off due to rubbing the cable against the flashtube along with the movement of the cable. A second embodiment of the disclosure may solve the above identified problems. With reference to FIGS. 14 to 21, a configuration of a surgical instrument 40 according to a second embodiment of the disclosure is described.

Figure 14:
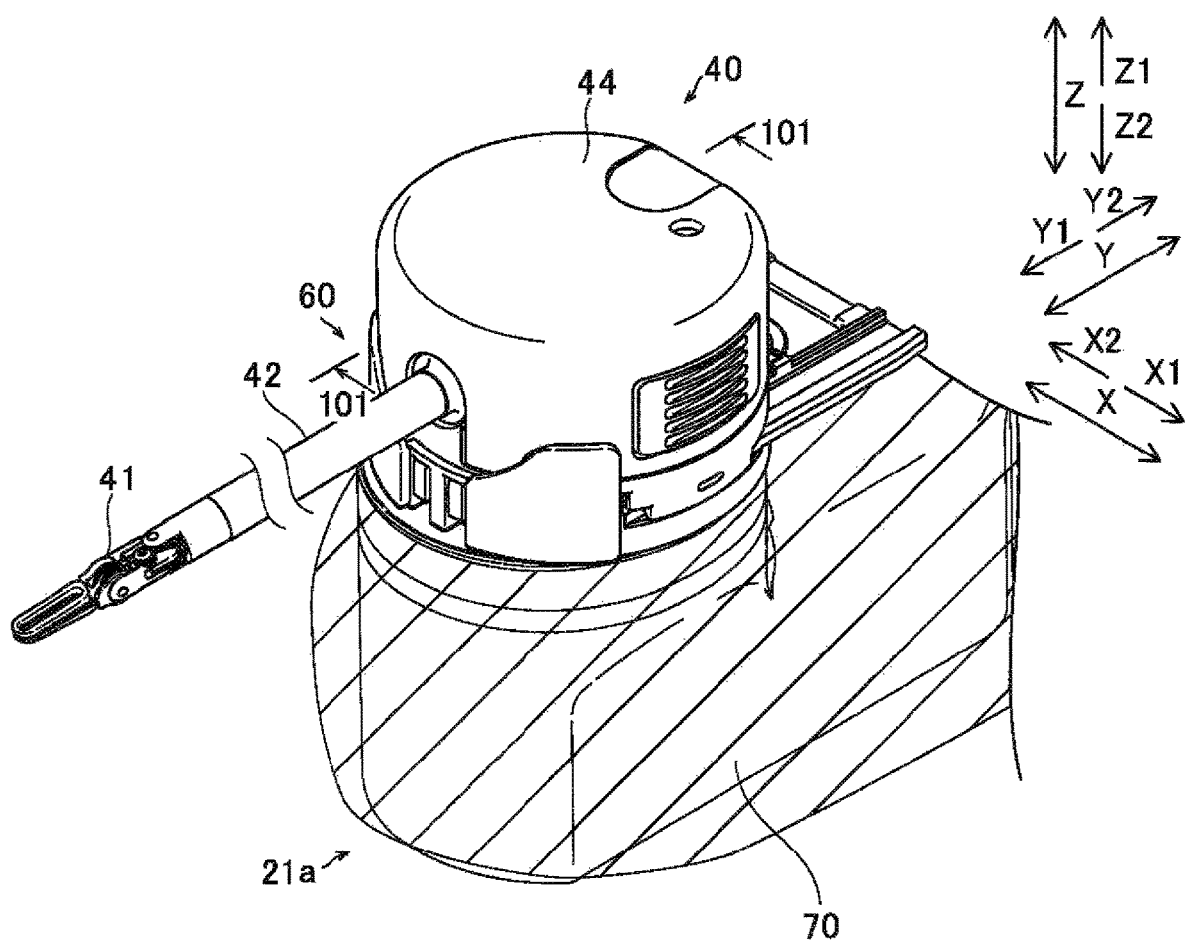
FIG. 14 is a diagram illustrating a perspective view of a state where a surgical instrument is attached to a robot arm via an adaptor according to a second embodiment.

As illustrated in FIG. 14, the surgical instrument 40 is detachably attached to the robot arm 21a of the robotic surgical system 100. The robot arm 21a is used in a clean area and is thus covered with the drape 70. In operation rooms, clean technique is used in order to prevent surgical incision sites and the medical equipment from being contaminated by pathogen, foreign matters, or the like. The clean technique defines a clean area and a contaminated area, which is outside the clean area. The surgery sites are located in the clean area. Members of the surgical team, including the operator, make sure that only sterile objects are placed in the clean area during surgery and perform sterilization for an object which is to be moved to the clean area from the contaminated area. Similarly, when the members of the surgical team including the operator place their hands in the contaminated area, the members sterilize their hands before directly touching objects located in the clean area. Instruments used in the clean area are sterilized or are covered with sterile drape 70.

The drape 70 is arranged between the robot arm 21a and the surgical instrument 40. Specifically, the drape 70 is arranged between the adaptor 60 and the robot arm 21a. The adaptor 60 is attached to the robot arm 21a while putting the drape 70 between the adaptor 60 and the robot arm 21a. Specifically, the adaptor 60 is the drape adaptor that puts the drape 70 between the adaptor 60 and the robot arm 21a. The drape 70 is thus able to be mounted through the adaptor 60. The surgical instrument 40 is attached to the adaptor 60 that is attached to the robot arm 21a with the drape 70 interposed therebetween. The robot arm 21a transmits driving force to the surgical instrument 40 through the adaptor 60 to drive the end effector 41 of the surgical instrument 40.

The direction in which the surgical instrument 40 and the adaptor 60 are adjacent to each other is referred to as the Z direction (Z axis), the surgical instrument 40 side in the Z direction is referred to as the Z1 side, and the adaptor 60 side in the Z direction is referred to as the Z2 side. Also, the direction in which the shaft 42 extends is defined as the Y direction (Y axis), the distal side of the shaft 42 in the Y direction is defined as the Y1 side, and the opposite side of the Y1 side is defined as the Y2 side. Also, the direction orthogonal to the Y direction and the Z direction is referred to as the X direction (X axis), one side along the X direction is referred as the X1 side, and the other side along the X direction is referred to as the X2 side.

Figure 15:
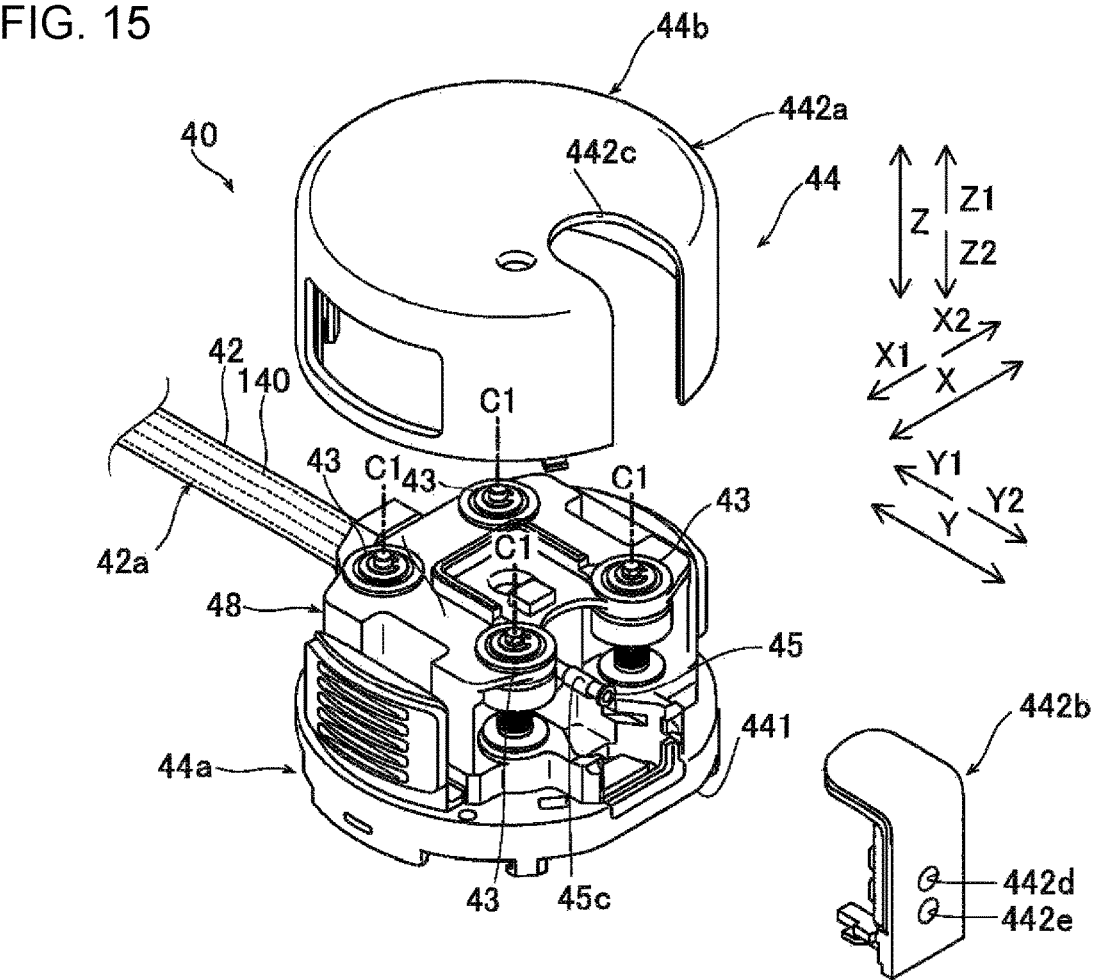
FIG. 15 is a diagram illustrating a perspective view of a state where a first lid portion and a second lid portion are detached from a base according to a second embodiment.

As illustrated FIG. 15, the surgical instrument 40 includes the shaft 42, the end effector 41 (see FIG. 14), and the housing 44.

(Housing)

As illustrated in FIG. 15, the housing 44 constitutes a casing or housing part that accommodates therein a drive mechanism of the surgical instrument 40. Specifically, the housing 44 includes the base 44a, a retaining member 48, the plural (four) driven members 43, the lid portion 44b, the cleaning tube 45, and a movement restriction portion 45c.

The base 44a is formed with the adaptor attachment surface 441 on the Z2 side of the base 44a. The adaptor attachment surface 441 is the attachment surface at which the surgical instrument 40 is attached to the robot arm 21a via the adaptor 60. To the base 44a, the other end of the shaft 42 is connected. The retaining member 48 holds the driven members 43 to be rotatable on the base 44a. The adaptor attachment surface 441 is an example of an "attachment surface."

The plural driven members 43 are driven by a driving part provided to the robot arm 21a to rotate about rotational axes C1 thereof. The plural driven members 43 are configured to move the wires 140 (elongate elements 42a) in the Y1 direction or the Y2 direction, by being rotated about the rotational axes C1 thereof. The driven members 43 are configured to move the wires 140 in the Y1 direction or the Y2 direction to drive the end effector 41 (see FIG. 14). Specifically, the end effector 41 is provided on the Y1 side of the shaft 42. The end effector 41 is connected to the shaft 42 via a support member. The base 44a of the housing 44 is connected to the Y2 side of the shaft 42. The driven members 43 are connected to the end effector 41 with the wires 140 passing through the shaft 42.

As described above, the surgical instrument 40 includes the wires 140 as the elongate elements 42a, inserted in the shaft 42 to operate the end effector 41.

With this configuration, the structure for operating the end effector 41 can be a simple structure, since the end effector 41 is operable by moving the elongate elements 42a such as the wires 140.

The shaft 42 is rotated by the rotation of one of the four driven members 43. The end effector 41 is driven by the rotation of the other three driven members 43. The four driven members 43 are arranged in two rows in the X direction and two columns in the Y direction. The driven members 43 are provided in the housing 44.

The lid portion 44b covers the base 44a from the Z1 side. The lid portion 44b includes the first lid portion 442a and the second lid portion 442b. The first lid portion 442a is detachably attached to the base 44a. The first lid portion 442a is formed with the notch 442c (a cutout or a removed portion) for disposing the second lid portion 442b. The notch 442c is formed on the portion of the first lid portion 442a on the Y2-side. The second lid portion 442b is detachably attached to the base 44a. The second lid portion 442b is detachably fit to the notch 442c of the first lid portion 442a. The second lid portion 442b includes a first cleaning liquid supply hole 422d and a second cleaning liquid supply hole 442e. Note that the first cleaning liquid supply hole 442d is an example of a "cleaning liquid supply hole".

Figure 16:
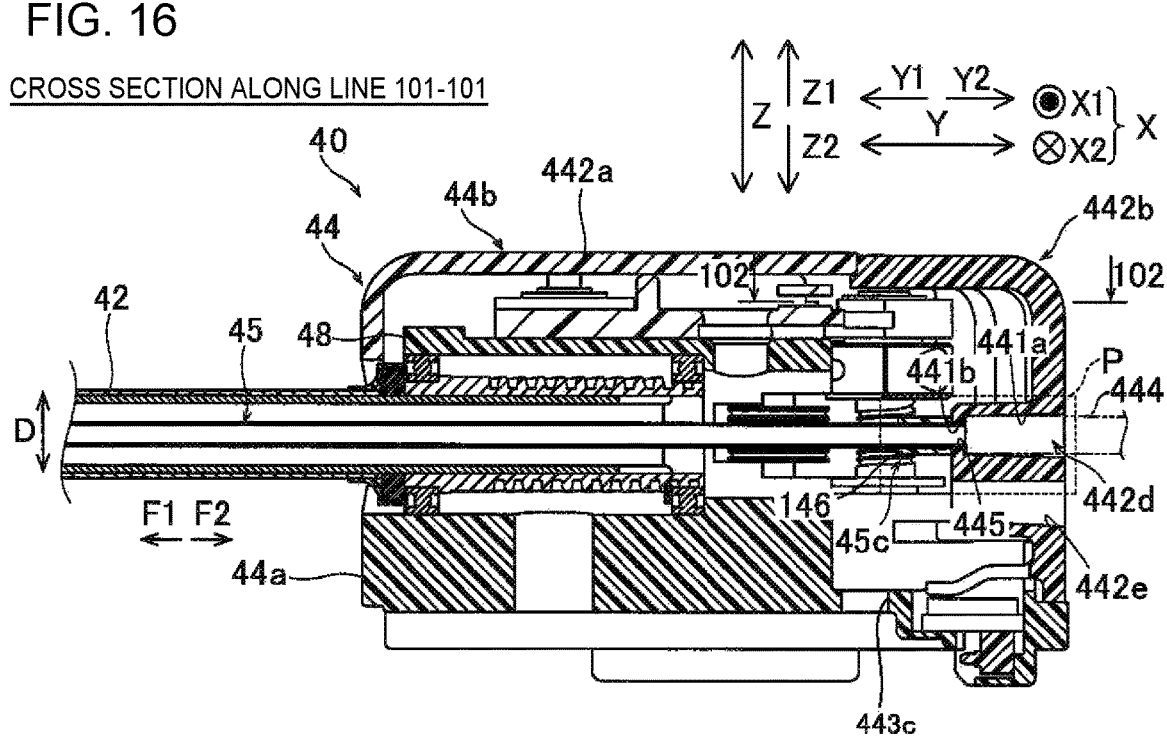
FIG. 16 is a diagram illustrating a cross-sectional view taken along the 101-101 line in FIG. 14.

As illustrated in FIGS. 15 and 16, the first cleaning liquid supply hole 442d and the second cleaning liquid supply hole 442e are provided to supply a cleaning liquid (such as water). The first cleaning liquid supply hole 442d and the second cleaning liquid supply hole 442e are the through holes penetrating the second lid portion 442b in the Y direction. The first cleaning liquid supply hole 442d and the second cleaning liquid supply hole 442e are arranged side by side in the Z direction. The first cleaning liquid supply hole 442d on the Z1 side is provided to supply the cleaning liquid to the inside of the shaft 42. The second cleaning liquid supply hole 442e on the Z2 side is provided to supply the cleaning liquid to the inside of the housing 44. The first cleaning liquid supply hole 442d includes a large diameter portion 441a for inserting (connecting) an end portion of a cleaning device 444 such as a syringe or a flushing tube for supplying the cleaning liquid, and a small diameter portion 441b provided on the Y1 side of the large diameter portion 441a (F1 side, described later) and having a diameter smaller than the large diameter portion 441a. The small diameter portion 441b is defined by an inner circumferential surface of a projected portion 445 protruded from an inner circumferential surface of the large diameter portion 441a toward the center line of the first cleaning liquid supply hole 442d. The projected portion 445 is provided at an end portion of the first cleaning liquid supply hole 442d on the Y1 side.

As described above, the lid portion 44b includes: the first lid portion 442a; and the second lid portion 442b that is attached to the first lid portion 442a, arranged on the side (Y2 side) opposite to the shaft 42 side in the Y direction (the axial direction of the shaft 42), and formed with the first cleaning liquid supply hole 442d. The second lid portion 442b is formed with the first cleaning liquid supply hole 442d to which the cleaning tube 45 is attached so that the cleaning tube 45 communicates with the first cleaning liquid supply hole 442d.

With this configuration, after the cleaning tube 45 is attached to the first cleaning liquid supply hole 442d of the second lid portion 442b to communicate with the first cleaning liquid supply hole 442d, the second lid portion 442b is attached to the first lid portion 442a while the cleaning tube 45 is being inserted into the shaft 42. Therefore, the surgical instrument 40 can be assembled efficiently.

Figure 17:
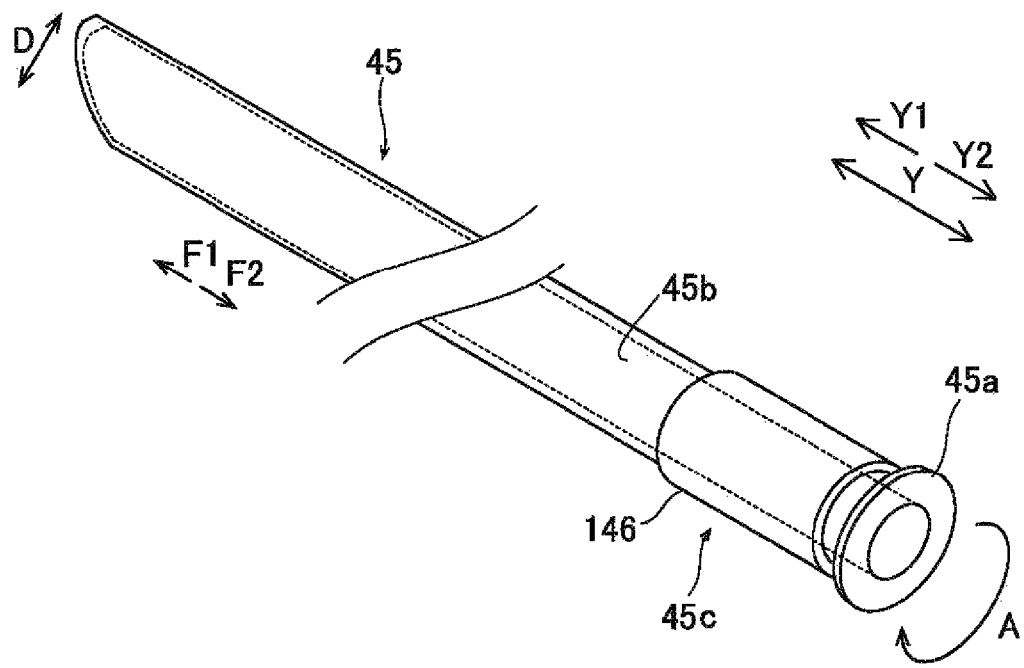
FIG. 17 is a diagram illustrating a perspective view of a cleaning tube of the surgical instrument with a heat-shrinkable tube being fixed thereto according to a second embodiment.

As illustrated in FIGS. 16 and 17, the cleaning tube 45 is configured to allow the cleaning liquid that is supplied to the first cleaning liquid supply hole 442d to flow to the distal end portion of the shaft 42.

Specifically, the cleaning tube 45 is provided so as to extend linearly along the Y direction (the axial direction of the shaft 42).

Accordingly, since the cleaning tube 45 extends linearly along the Y direction (the axial direction of the shaft 42), the momentum of the cleaning liquid flowing in the cleaning tube 45 can be maintained, unlike a case where the cleaning tube 45 is bent in the middle. Also, since the cleaning tube 45 extends linearly along the Y direction (the axial direction of the shaft 42), it is not necessary to provide a holding member for holding the cleaning tube 45 in a bent posture and thus the surgical instrument 40 can be made compact, unlike the case where the cleaning tube 45 is bent in the middle.

The cleaning tube 45 has a cylindrical shape. The cleaning tube 45 is a resin tube extending along the Y direction. Specifically, the cleaning tube 45 is made of a fluorine resin material. A portion of the cleaning tube 45 on the Y2 side is inserted into the first cleaning liquid supply hole 442d. A portion of the cleaning tube 45 on the Y1 side is inserted into the shaft 42.

The cleaning tube 45 includes a flange portion 45a. The flange portion 45a has a function of preventing the cleaning tube 45 from coming off from the first cleaning liquid supply hole 442d toward the Y1 side. The flange portion 45a protrudes from an outer circumferential surface 45b of the cleaning tube 45 in the radial direction of the cleaning tube 45 (hereinafter referred to as a D direction). The flange portion 45a is provided on an end portion of the cleaning tube 45 on the Y2 side.

Figure 18:
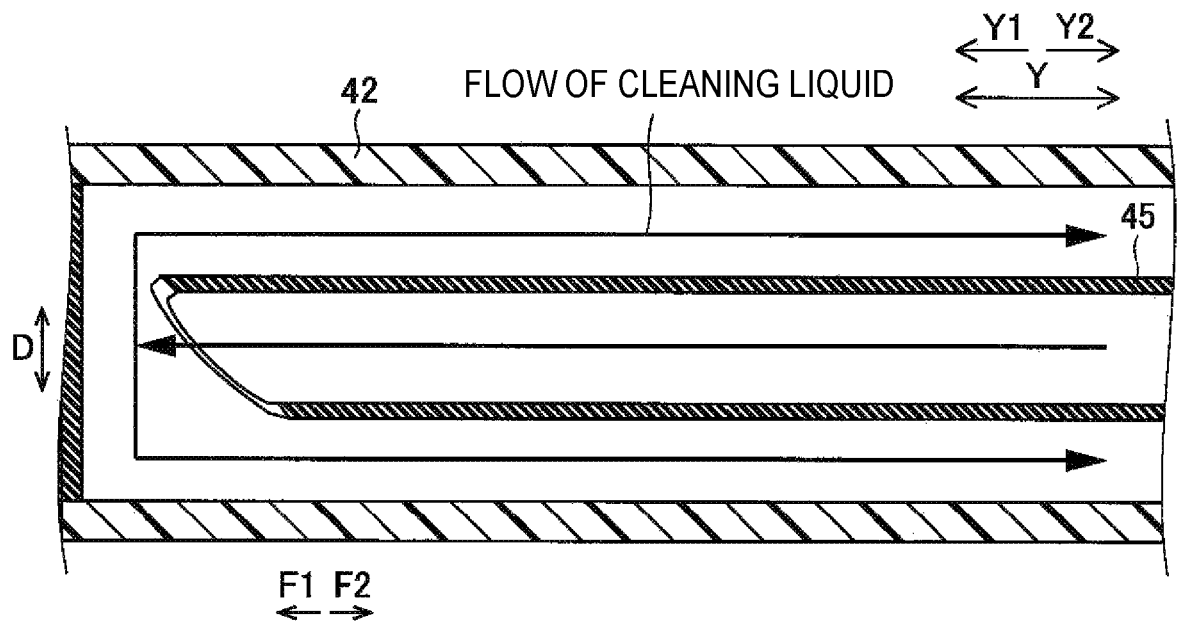
FIG. 18 is a diagram illustrating a cross sectional view of a distal end portion of the cleaning tube inserted in a shaft of the surgical instrument according to a second embodiment.

As illustrated in FIG. 18, the Y1-side end portion of the cleaning tube 45 is inserted all the way to a position in the vicinity of the distal end of the shaft 42 on the Y1 side. The cleaning liquid supplied from the first cleaning liquid supply hole 442d flows in the cleaning tube 45 and then flows out from the distal end portion of the cleaning tube 45. The cleaning liquid flowing out from the distal end portion of the cleaning tube 45 flows into the shaft 42 and then flows from the Y1-side end of the shaft 42 toward the Y2-side end of the shaft 42. Then, the cleaning liquid flows out into the housing 44 from the Y2-side end of the shaft 42, and then flows out from the housing 44 though the gaps existing in the housing 44 as discharge holes (not illustrated). In this way, the inside of the shaft 42 is cleaned.

(Movement Restriction Portion)

Figure 19:
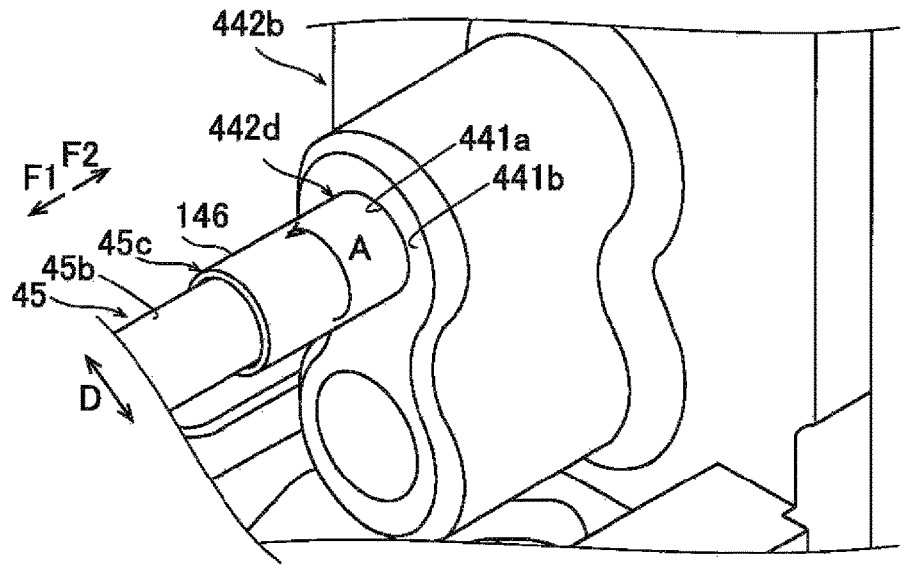
FIG. 19 is a diagram illustrating a perspective view of a portion in the vicinity of the heat-shrinkable tube of the surgical instrument according to a second embodiment.
Figure 20:
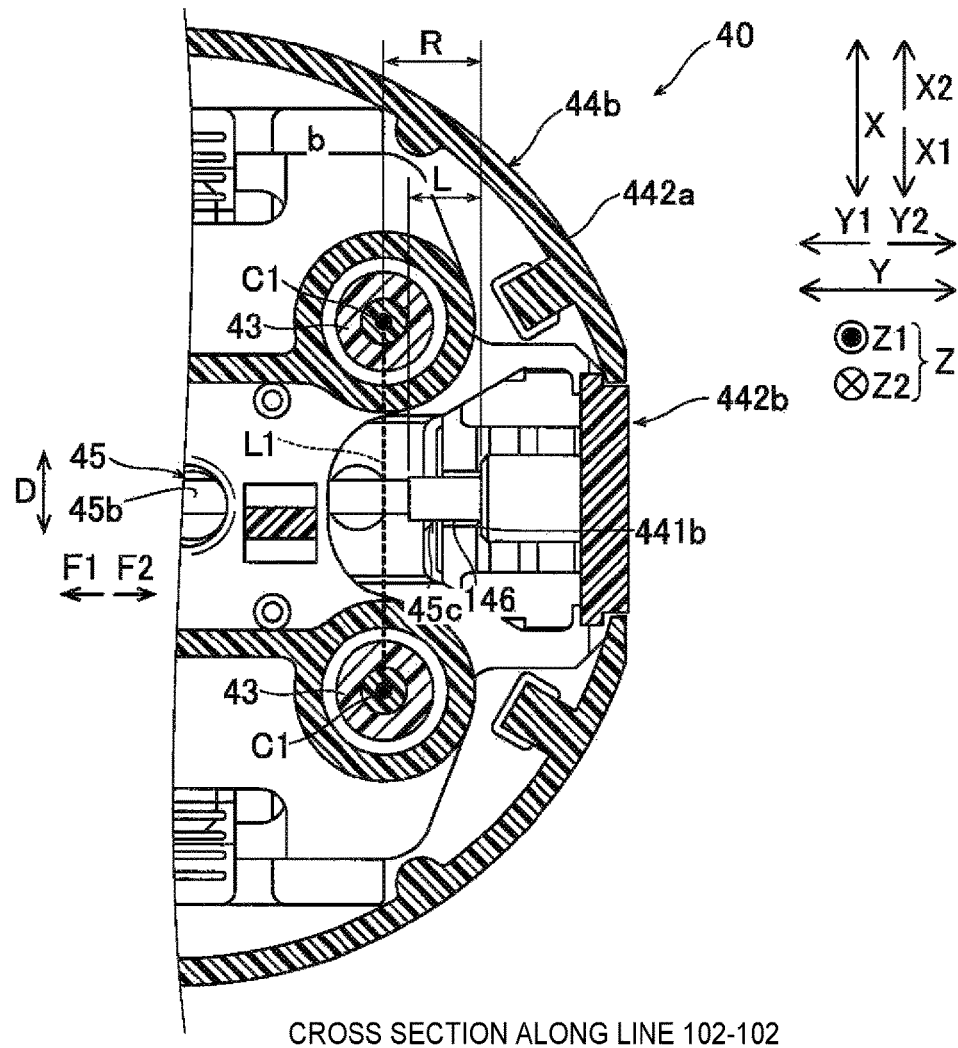
FIG. 20 is a diagram illustrating a cross-sectional view taken along the 102-102 line in FIG. 16.

As illustrated in FIGS. 19 and 20, the surgical instrument 40 according to a second embodiment is provided with a movement restriction portion 45c, in order to restrict the movement of the cleaning tube 45 in the Y2 direction due to the pressure of the cleaning liquid that flows from the Y1-side end of the shaft 42 to the Y2-side end of the shaft 42. That is, the movement restriction portion 45c has a function as a retaining member. Specifically, the movement restriction portion 45c is configured to abut on the second lid portion 442b so as to restrict the movement of the cleaning tube 45 in the X2 direction.

Accordingly, the surgical instrument 40 includes: the shaft 42; the end effector 41 provided on the side of the one end of the shaft 42; and the housing 44 that is provided on the side of the other end of the shaft 42 and that includes the base 44a including the adaptor attachment surface 441 to be attached to the robot arm 21a and the lid portion 44b covering the base 44a. The lid portion 44b (specifically, the second lid portion 442b) is provided with the first cleaning liquid supply hole 442d to supply the cleaning liquid. The cleaning tube 45 for supplying the cleaning liquid into the shaft 42 is attached to the first cleaning liquid supply hole 442d so that the cleaning tube 45 communicates with the first cleaning liquid supply hole 442d. The movement restriction portion 45c is provided on the outer circumferential surface 45b of the cleaning tube 45, to restrict the movement of the cleaning tube 45 in a direction (hereinafter may be referred to as an F2 direction) opposite to a direction of flow of the cleaning liquid in the cleaning tube 45 (hereinafter may be referred to as an F1 direction, a cleaning liquid supply direction). Note that the F1 and F2 directions are parallel to the Y direction.

With this configuration, regardless of the layout of the cleaning tube 45, the movement restriction portion 45c can restrict the movement of the cleaning tube 45 in the F2 direction (opposite to the cleaning liquid supply direction in the cleaning tube) due to the pressure of the cleaning liquid supplied from the cleaning tube 45 to the inside of the shaft 42. The movement of the cleaning tube 45 in the F2 direction can be restricted by the movement restriction portion 45c, even when the end effector 41 is operated by the wire 140 passing through the shaft 42 and the wire 140 rubs against the cleaning tube 45 along with the movement of the wire 140 and thus the force is applied to the cleaning tube 45 in the F2 direction (the direction opposite to the cleaning liquid supply direction). As a result, it is possible to reliably prevent the cleaning tube 45 from coming off the housing 44.

Figure 21:
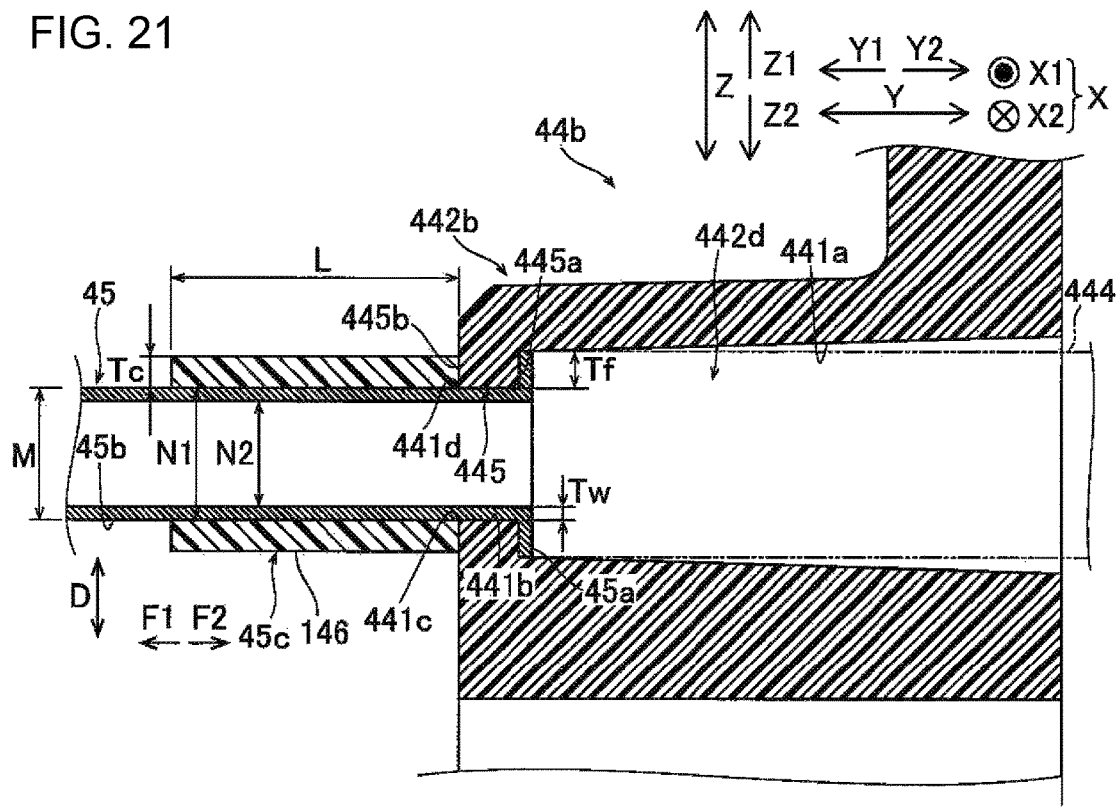
FIG. 21 is a diagram illustrating an enlarged view of the P part in FIG. 16.
Figure 22:
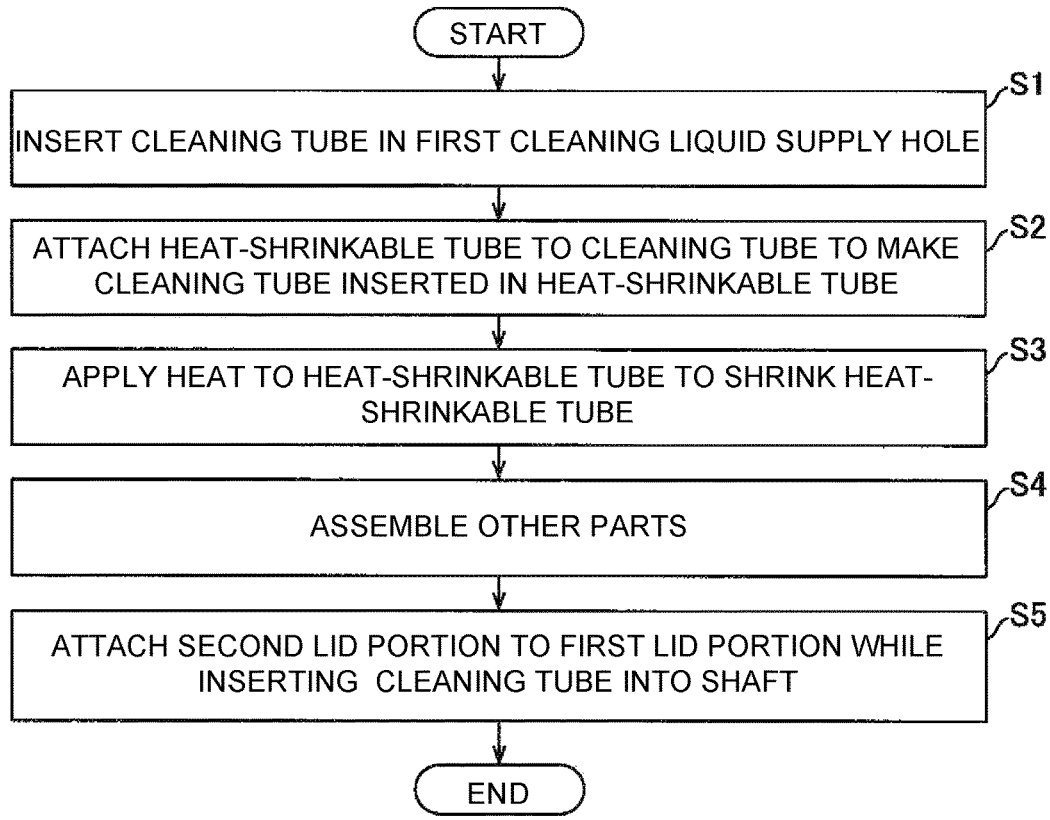
FIG. 22 is a diagram illustrating a flowchart of a method of assembling the surgical instrument according to a second embodiment.

Specifically, as illustrated in FIGS. 20 and 21, the movement restriction portion 45c is in contact with a peripheral edge portion 441d of an opening 441c (downstream-side opening 441c) of the first cleaning liquid supply hole 442d of the second lid portion 442b on the downstream side in the F1 direction (the cleaning liquid supply direction).

According to this configuration, the movement restricting portion 45c is in contact with the peripheral edge portion 441d of the downstream-side opening 441c of the first cleaning liquid supply hole 442d of the second lid portion 442b. Thus, the movement of the cleaning tube 45 in the F2 direction (the direction opposite to the cleaning liquid supply direction) can be reliably restricted. Therefore, it is possible to reliably prevent the cleaning tube 45 from coming off the housing 44.

Here, the downstream-side opening 441c of the first cleaning liquid supply hole 442d is an F1-side opening of the small diameter portion 441b, which is reduced in diameter by the projected portion 445 of the first cleaning liquid supply hole 442d. Further, the peripheral edge portion 441d of the opening 441c is a portion of an F1-side surface 445b of the projected portion 445 in the vicinity of the opening 441c.

Also, the movement of the cleaning tube 45 is restricted not only in the F2 direction but also in the F1 direction. That is, the surgical instrument 40 has a retaining structure for preventing the cleaning tube 45 from coming out from the first cleaning liquid supply hole 442d both to the outside of the housing 44 and to the inside of the housing 44.

Specifically, the first cleaning liquid supply hole 442d includes the large diameter portion 441a to which the tip end portion of the cleaning device 444 for supplying the cleaning liquid is to be inserted, and the small diameter portion 441b provided on the F1 side (the side of the cleaning liquid supply direction) of the large diameter portion 441a and being smaller than the large diameter portion 441a in diameter. The lid portion 44b (specifically, the second lid portion 442b) includes the projected portion 445 protruded from the inner circumferential surface of the large diameter portion 441a toward the center of the first cleaning liquid supply hole 442d and forming the small diameter portion 441b. The cleaning tube 45 includes the flange portion 45a outwardly protruding therefrom in the D direction (the radial direction of the cleaning tube 45). The movement restriction portion 45c and the flange portion 45a are arranged so as to sandwich the projected portion 445 in the F1 direction (the cleaning liquid supply direction).

With this configuration, by simply sandwiching the projected portion 445 between the movement restriction portion 45c and the flange portion 45a of the cleaning tube 45, the movement of the cleaning tube 45 in the F1 direction (the cleaning liquid supply direction) and in the F2 direction (the direction opposite to the cleaning liquid supply direction) can be restricted. Therefore, it is possible to suppress the complexity of the structure for restricting the movement of the cleaning tube 45 in the F1 direction (the cleaning liquid supply direction) and in the F2 direction (the direction opposite to the cleaning liquid supply direction).

In this way, the cleaning tube 45 is restricted from moving to the downstream side, by the flange portion 45a being in contact with the upstream-side surface 445a of the projected portion 445 in the F1 direction (the cleaning liquid supply direction). The cleaning tube 45 is restricted from moving to the upstream side, by the movement restriction portion 45c being in contact with the downstream-side surface 445b of the projected portion 445 in the F1 direction (the cleaning liquid supply direction).

With this configuration, the movement of the cleaning tube 45 in both the F1 direction (the cleaning liquid supply direction) and the F2 direction (the direction opposite to the cleaning liquid supply direction) can be restricted. Accordingly, it is possible to prevent the cleaning tube 45 from slipping out into the housing 44 due to the cleaning tube 45 moving in the F1 direction (the cleaning liquid supply direction) and also to prevent the cleaning tube 45 from coming out of the housing 44 due to the cleaning tube 45 moving in the F2 direction (the direction opposite to the cleaning liquid supply direction).

In a second embodiment, the movement restriction portion 45*c* is an attachment member (a heat-shrinkable tube 146, described later) attached to the outer circumferential surface 45*b* of the cleaning tube 45.

With this configuration, the movement of the cleaning tube 45 can be restricted without changing the shape of the cleaning tube 45, unlike a case where the cleaning tube 45 is integrally provided with a projected portion (the movement restriction portion 45*c*) protruding in the D direction (the radial direction of the cleaning tube 45). Therefore, an existing (general-purpose) cleaning tube can be used as it is for the cleaning tube 45.

The attachment member has a tubular shape fixed so as to surround (cover) the cleaning tube 45 in the circumferential direction (A direction (see FIG. 19)) of the cleaning tube 45.

With this configuration, the attachment member can be fixed to the entire circumference of the outer circumferential surface 45*b* of the cleaning tube 45, so that the attachment member can be firmly fixed to the cleaning tube 45.

The attachment member is the heat-shrinkable tube (heat-shrinking tube) 146.

With this configuration, since the heat-shrinkable tube 146 shrinks when heated, the heat-shrinkable tube 146 can be fixed to the cleaning tube 45 without using an adhesive or the like. Therefore, it may be not necessary to perform the inspection (validation) required for fixing with an adhesive. As a result, without inspecting the fixing of the heat-shrinkable tube 146 to the cleaning tube 45, it is possible to suppress the complexity of the assembling work of the surgical instrument 40.

The heat-shrinkable tube 146 is a resin tube extending along the Y direction. Specifically, the heat-shrinkable tube 146 is made of a fluorine resin material that is different from that of the cleaning tube 45. The heat-shrinkable tube 146 is made of a material that becomes harder than the cleaning tube 45 when heated. The heat-shrinkable tube 146 may be made of any material as long as it is a material that shrinks when heated.

The heat-shrinkable tube 146 has a thickness Tc in the D direction. The thickness Tc of the heat-shrinkable tube 146 in the cured state is less than the thickness Tf of the flange portion 45*a* in the D direction. The thickness Tc of the heat-shrinkable tube 146 in the cured state is greater than the thickness Tw of the cleaning tube 45 in the D direction.

The heat-shrinkable tube 146 is in close contact with the outer circumferential surface 45*b* of the cleaning tube 45 in the D direction. That is, the heat-shrinkable tube 146 is in contact with the cleaning tube 45 in the D direction. A contact area for tightening the cleaning tube 45 by the heat-shrinkable tube 146 is an area obtained by multiplying the circumferential length of the heat-shrinkable tube 146 along the A direction by the length of the heat-shrinkable tube 146 in the F1 direction (the axis direction of the heat-shrinkable tube 146).

The heat-shrinkable tube 146 tightens the cleaning tube 45 in the state where the heat-shrinkable tube 146 is harder than the cleaning tube 45 due to heat shrinkage.

With this configuration, deflection of the heat-shrinkable tube 146 due to the force applied from the outside can be suppressed, compared to a case where the heat-shrinkable tube 146 has a hardness less than the cleaning tube 45. Therefore, the heat-shrinkable tube 146 can be prevented from coming off the cleaning tube 45 due to the force applied from the outside.

The heat-shrinkable tube 146 tightens the cleaning tube 45 by being heated and shrunken in diameter. With this, the heat-shrinkable tube 146 is fixed to the cleaning tube 45 at a certain position. The tightening force of the heat-shrinkable tube 146 is set based on the inner diameter N1 of the cured heat-shrinkable tube 146 and the length L of the heat-shrinkable tube 146 in the F1 direction.

The inner diameter N1 of the cured heat-shrinkable tube 146 is set in such a manner that the inner diameter N2 of the portion of the cleaning tube 45 where the cured heat-shrinkable tube 146 is arranged is not excessively smaller than the inner diameter of the other portion of the cleaning tube 45. That is, in the D direction, the inner diameter N1 of the cured heat-shrinkable tube 146 is slightly smaller than the outer diameter M of the cleaning tube 45 before being tightened by the cured heat-shrinkable tube 146. With this configuration, the heat-shrinkable tube 146 can be reliably fixed to the cleaning tube 45 without obstructing the flow of the cleaning liquid at the portion of the cleaning tube 45 where the heat-shrinkable tube 146 is arranged.

The length L of the heat-shrinkable tube 146 in the F1 direction (the cleaning liquid supply direction) is equal to or greater than the outer diameter M of the cleaning tube 45 in the D direction (the radial direction, the direction orthogonal to the cleaning liquid supply direction).

With this configuration, the heat-shrinkable tube 146 can be firmly fixed to the cleaning tube 45, since the contact area between the heat-shrinkable tube 146 and the cleaning tube 45 can be sufficiently secured.

Further, the length L of the heat-shrinkable tube 146 in the F1 direction is set such that the heat-shrinkable tube 146 does not interfere with the wires 140 inserted into the shaft 42 from the driven members 43. Specifically, the length L of the heat-shrinkable tube 146 in the F1 direction is less than the distance R from the Y1-side end of the first cleaning liquid supply hole 442*d* to the line L1 connecting the rotation axes C1 of two driven members 43 located on the Y2 side.

In this way, the end portion of the heat-shrinkable tube 146 on the side of the first cleaning liquid supply hole 442*d* is positioned at the Y1-side end portion of the first cleaning liquid supply hole 442*d*. Specifically, in the F1 direction, the end portion of the heat-shrinkable tube 146 on the side of the shaft 42 is positioned in the vicinity of the line L1a connecting the rotation axes C1 of the two driven members 43 located on the Y2 side.

The cleaning tube 45 is press-fitted into and attached to the first cleaning liquid supply hole 442*d*.

With this configuration, the movement of the cleaning tube 45 in the F2 direction is restricted not only by the movement restriction portion 45*c* but also by press-fitting the cleaning tube 45 in the first cleaning liquid supply hole 442*d*. Accordingly, it is possible to prevent the cleaning tube 45 from coming off during the cleaning operation of the shaft 42 more reliably.

Specifically, the cleaning tube 45 is tightened from the outer side in the D direction by the projected portion 445 of the second lid portion 442*b*.

(Method of Assembling Surgical Instrument)

Hereinafter, a method of assembling the surgical instrument 40 is described with reference to FIGS. 22 to 25. The method of assembling the surgical instrument 40 includes a step of attaching the heat-shrinkable tube 146 to the cleaning tube 45.

Figure 23:
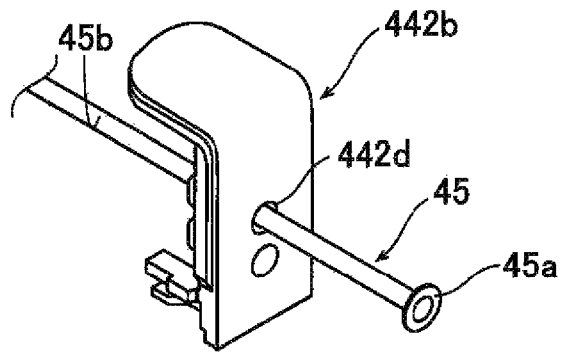
FIG. 23 is a diagram illustrating a perspective view of a state where the cleaning tube of the surgical instrument is inserted into a first cleaning liquid supply hole of the second lid portion according to a second embodiment.
Figure 24:
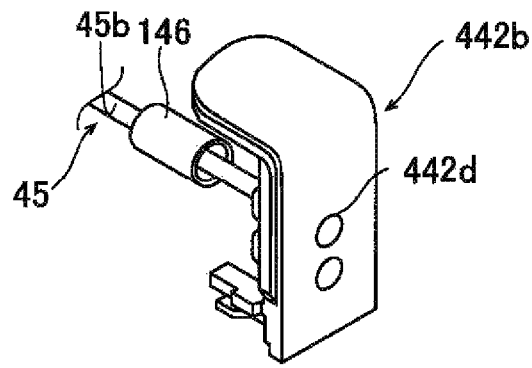
FIG. 24 is a diagram illustrating a perspective view of a state where the heat-shrinkable tube is attached to the cleaning tube in such a manner that the cleaning tube is inserted in the heat-shrinkable tube in the surgical instrument according to a second embodiment.

In step S1, a worker inserts the cleaning tube 45 into the first cleaning liquid supply hole 442*d* (see FIG. 23). At this time, the worker inserts the cleaning tube 45 into the first cleaning liquid supply hole 442d until the flange portion 45a of the cleaning tube 45 comes in contact with the upstream-side surface 445a (see FIG. 21) of the projected portion 445. In step S2, the worker attaches the heat-shrinkable tube 146 to the cleaning tube 45 in such a manner that the cleaning tube 45 is inserted in the heat-shrinkable tube 146 (see FIG. 24). That is, the worker attaches the heat-shrinkable tube 146 to the cleaning tube 45 from the end portion of the cleaning tube 45 on the side opposite from the flange portion 45a of the cleaning tube 45, so that the cleaning tube 45 is inserted into the heat-shrinkable tube 146. At this time, the worker slides the heat-shrinkable tube 146 on the cleaning tube 45 until the heat-shrinkable tube 146 comes into contact with the downstream-side surface 445b of the projected portion 445 of the second lid portion 442b.

Figure 25:
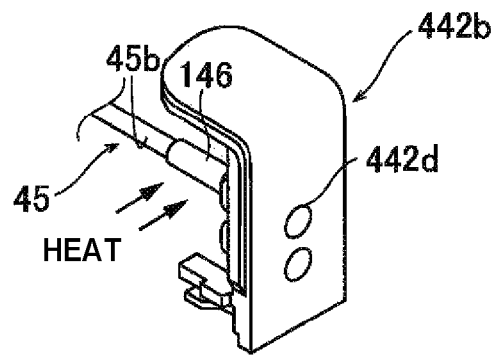
FIG. 25 is a diagram illustrating a perspective view of a state where the heat-shrinkable tube of the surgical instrument is shrunk by being heated according to a second embodiment.

In step S3, the worker applies heat to the heat-shrinkable tube 146 to shrink the heat-shrinkable tube 146 (see FIG. 25). With this, the heat-shrinkable tube 146 is fixed to the cleaning tube 45 in the state where the heat-shrinkable tube 146 is in contact with the second lid portion 442b.

In Step S4, the worker assembles other parts of the surgical instrument 40. Then, in step S5, the worker attaches the second lid portion 442b to the housing 44 (the first lid portion 442a) while inserting the cleaning tube 45 into the shaft 42. With this, the assembly work of the surgical instrument 40 is completed.

Modified Example

It should be noted that the embodiments disclosed herein are exemplary in all respects and are not considered to be restrictive. The scope of the invention is indicated by claims, not by explanation of the embodiments described above, and includes equivalents to the claims and all alterations (modification) within the same.

For example, in an embodiment described above, the case has been described in which the second cleaning liquid supply hole is provided to open in the axial direction of the shaft, and the third cleaning liquid supply hole is provided to open in the direction substantially orthogonal to the axial direction of the shaft. However, the disclosure is not limited thereto. In an embodiment, as long as a second cleaning liquid supply hole and a third cleaning liquid supply hole are substantially orthogonal to each other, the second cleaning liquid supply hole may be opened in a direction not parallel to an axial direction of a shaft or the third cleaning liquid supply hole may be opened in a direction not parallel to a direction substantially orthogonal to the axial direction of the shaft.

Further, in an embodiment described above, the case has been described in which the third cleaning liquid supply hole is provided at the base of the housing. However, the disclosure is not limited thereto. In the disclosure, a third cleaning liquid supply hole may be provided at a lid portion of a housing.

Further, in an embodiment described above, the case has been described in which the third cleaning liquid supply hole is provided at the position off the center of the base. However, the disclosure is not limited thereto. In the disclosure, a third cleaning liquid supply hole may be provided at a center of a base.

Further, in an embodiment described above, the case has been described in which the third cleaning liquid supply hole is provided at the position off the center of the base in the axial direction of the shaft. However, the disclosure is not limited thereto. In the disclosure, a third cleaning liquid supply hole may be provided at a position off a center of a base not only in an axial direction of a shaft, but also in a direction substantially orthogonal to the axial direction of the shaft and substantially parallel to an attachment surface of the base.

Further, in an embodiment described above, the case has been described in which the third cleaning liquid supply hole is provided at the portion of the base on the side opposite from the shaft side. However, the disclosure is not limited thereto. In the disclosure, a third cleaning liquid supply hole may be provided at a portion of a base on a shaft side.

Further, in an embodiment described above, the case has been described in which the first cleaning liquid supply hole, the second cleaning liquid supply hole, and the third cleaning liquid supply hole are provided in the same plane. However, the disclosure is not limited thereto. In the disclosure, first, second, and third cleaning liquid supply holes may not be provided in a same plane. In this case, the first, second, and third cleaning liquid supply holes may be provided in different planes, respectively, or, two of the first, second, and third cleaning liquid supply holes may be provided in a same plane and the other one may be provided in a plane different from the same plane.

Further, in an embodiment described above, the case has been described in which the first cleaning liquid supply hole, the second cleaning liquid supply hole, and the third cleaning liquid supply hole are provided one by one. However, the disclosure is not limited thereto. In the disclosure, at least one of the first, second, and third cleaning liquid supply holes may be plurally provided. For example, it may be configured such that one first cleaning liquid supply hole is provided, and a plurality of second cleaning liquid supply holes and a plurality of third cleaning liquid supply holes are provided. It may also be configured such that first and second cleaning liquid supply holes are provided one by one and a plurality of third cleaning liquid supply holes are provided.

Further, in an embodiment described above, the case has been described in which the first cleaning liquid supply hole is provided to open in the axial direction of the shaft. However, the disclosure is not limited thereto. In the disclosure, a first cleaning liquid supply hole may be opened in a direction other than an axial direction of a shaft. For example, a first cleaning liquid supply hole may be opened in a direction substantially orthogonal to an axial direction of a shaft.

Further, in an embodiment described above, the case has been described in which the lid portion includes the first portion (the first lid portion) and the second portion (the second lid portion) which are dividable from each other. However, the disclosure is not limited thereto. In the disclosure, a lid portion may be formed of a single member. That is, a lid portion may have an undividable structure.

Further, in an embodiment described above, the case has been described in which the four driven members are provided. However, the invention is not limited thereto. In the disclosure, the number of driven members provided may plural other than four.

Further, in an embodiment described above, the case has been described in which the explanation plate is made of aluminum. However, the invention is not limited to this. In the disclosure, an explanation plate may be made of metal other than aluminum. Even in a case where such an explanation plate is made of metal other than aluminum, that can be corroded by an alkaline detergent, the coating with the resin film according to an embodiment described above is effective.

In an embodiment described above, the case has been described in which the surgical instrument is the non-electric surgical instrument. However, the disclosure is not limited thereto. In the disclosure, a surgical instrument may be an electrosurgical instrument.

Further, in an embodiment described above, the case has been described in which the cleaning tube extends in the Y direction (the axial direction of the shaft). However, the disclosure is not limited thereto. In the disclosure, the cleaning tube may be bent in a direction(s) other than the axial direction of the shaft.

Further, in an embodiment described above, the case has been described in which the movement restriction portion is configured as the attachment member that is provided separately from the cleaning tube and is attached to the outer circumferential surface of the cleaning tube. However, the disclosure is not limited thereto. For example, in the disclosure, a movement restriction portion may be formed integrally with a cleaning tube.

Further, in an embodiment described above, the case has been described in which the attachment member has the tubular shape that surrounds the cleaning tube in the circumferential direction of the cleaning tube so as to be fixed to the cleaning tube. However, the disclosure is not limited thereto. In the disclosure, an attachment member may be a member having a C-shaped in the cross section thereof.

Further, in an embodiment described above, the case has been described in which the movement restriction portion is the heat-shrinkable tube. However, the disclosure is not limited to this. In the disclosure, a movement restriction portion may be a tubular member that is fixed to a cleaning tube with an adhesive.

Further, in an embodiment described above, the case has been described in which the cleaning tube is tightened by the heat-shrinkable tube in the state where the heat-shrinkable tube is harder than the cleaning tube by being heated and shrunk. However, the disclosure is not limited thereto. In the disclosure, a heat-shrinkable tube after being shrunk may be as hard as or softer than a cleaning tube.

Further, in an embodiment described above, the case has been described in which the length L of the heat-shrinkable tube in the F1 direction (the cleaning liquid supply direction in the cleaning tube) is equal to or greater than the outer diameter M of the cleaning tube in the D direction (the direction orthogonal to the cleaning liquid supply direction). In the disclosure, a length of a heat-shrinkable tube in a cleaning liquid supply direction in a cleaning tube may be less than an outer diameter of the cleaning tube in a direction orthogonal to the cleaning liquid supply direction.

Further, in an embodiment described above, the case has been described in which the cleaning tube is press-fitted and attached to the first cleaning liquid supply hole (the cleaning liquid supply hole). However, the disclosure is not limited thereto. In the disclosure, a cleaning tube may not be press-fitted into and attached to a cleaning liquid supply hole.

Further, in an embodiment described above, the case has been described in which the movement restriction portion abuts on the peripheral edge portion of the downstream-side opening of the first cleaning liquid supply hole (the cleaning liquid supply hole) in the F1 direction (the cleaning liquid supply direction). However, the disclosure is not limited thereto. In the disclosure, a movement restriction portion may be provided in a position away from a peripheral edge portion of a downstream-side opening of a cleaning liquid supply hole.

Further, in the embodiment described above, the case has been described in which the second lid portion is formed with the first cleaning liquid supply hole (the cleaning liquid supply hole) to which the cleaning tube is attached so as to communicate with the first cleaning liquid supply hole. However, the disclosure is not limited thereto. In the disclosure, a cleaning liquid supply hole may be formed at a first lid portion.

Further, in an embodiment described above, the case has been described in which the F1 direction (the cleaning liquid supply direction in the cleaning tube) and the F2 direction (the direction opposite to the cleaning liquid supply direction) are parallel to the Y direction (the axial direction of the shaft). However, the disclosure is not limited thereto. In the disclosure, a cleaning liquid supply direction in a cleaning tube and a direction opposite to the cleaning liquid supply direction may not be parallel to an axial direction of a shaft.

Further, in an embodiment described above, the case has been described in which the elongate elements to drive the end effector are the wires. However, the invention is not limited thereto. In the disclosure, an elongate element may be a cable, a rod, or the like.

The invention claimed is:

1. A surgical instrument comprising:
    a shaft;
    an end effector provided on a side of one end of the shaft;
    a housing including: a base provided on a side of the other end of the shaft and including an attachment surface at which the base is to be attached to a robot arm; a lid portion covering the base; and cleaning liquid supply holes to supply a cleaning liquid; and
    a cleaning tube provided in the housing, extending from an inside of the housing to an inside of the shaft, and configured to supply the cleaning liquid to the inside of the shaft, wherein
    the cleaning liquid supply holes comprise: a first cleaning liquid supply hole to which the cleaning tube is attached; a second cleaning liquid supply hole communicating with the inside of the housing; and a third cleaning liquid supply hole opening in a direction substantially orthogonal to an opening direction of the second cleaning liquid supply hole and communicating with the inside of the housing,
    the cleaning tube comprises an insertion portion and a movement restriction portion arranged on an outer circumferential surface of the cleaning tube, the movement restriction portion adjacent to an end of the cleaning tube on a housing side thereof, the movement restriction portion having a larger outer diameter than an outer diameter of the insertion portion, and
    the cleaning tube further comprises a flange at the end of the cleaning tube on the housing side thereof such that the first cleaning liquid supply hole is arranged between the movement restriction portion and the flange of the cleaning tube, the flange having an outer diameter larger than the outer diameter of the insertion portion and a diameter of the first cleaning liquid supply hole, the flange preventing a movement of the cleaning tube away from the first cleaning liquid supply hole in a direction of supplying the cleaning liquid in the cleaning tube.

2. The surgical instrument according to claim 1, wherein the second cleaning liquid supply hole is provided opening in an axial direction of the shaft, and
    the third cleaning liquid supply hole is provided opening in the direction substantially orthogonal to the axial direction of the shaft.

3. The surgical instrument according to claim 2, wherein the third cleaning liquid supply hole is provided in the base.

4. The surgical instrument according to claim 3, wherein the third cleaning liquid supply hole is provided at the attachment surface of the base, in such a manner that the third cleaning liquid supply hole is provided opening in the direction substantially orthogonal to the attachment surface of the base.

5. The surgical instrument according to claim 4, wherein the third cleaning liquid supply hole is provided at a position off a center of the base.

6. The surgical instrument according to claim 5, wherein the third cleaning liquid supply hole is provided at the position off the center of the base in the axial direction of the shaft.

7. The surgical instrument according to claim 5, wherein the third cleaning liquid supply hole is provided at a portion of the base on a side opposite from a side of the shaft.

8. The surgical instrument according to claim 1, wherein the first, second, and third cleaning liquid supply holes are provided in a same plane.

9. The surgical instrument according to claim 8, wherein the first, second, and third cleaning liquid supply holes are provided in the same plane that passes an axis of the shaft.

10. The surgical instrument according to claim 1, wherein the first, second, and third cleaning liquid supply holes are provided one each.

11. The surgical instrument according to claim 1, wherein
the lid portion is formed with the first cleaning liquid supply hole to which the cleaning tube is attached in such a manner that the first cleaning liquid supply hole communicates with the cleaning tube, and
the outer circumferential surface of the cleaning tube is formed with the movement restriction portion that restricts a movement of the cleaning tube in a direction opposite to the direction of supplying the cleaning liquid in the cleaning tube.

12. The surgical instrument according to claim 11, wherein
the cleaning tube is provided so as to extend in an axial direction of the shaft.

13. The surgical instrument according to claim 11, wherein
the movement restriction portion is formed of an attachment member attached to the outer circumferential surface of the cleaning tube.

14. The surgical instrument according to claim 13, wherein
the attachment member has a tubular shape surrounding the cleaning tube along a circumferential direction of the cleaning tube.

15. The surgical instrument according to claim 14, wherein
the attachment member is a heat-shrinkable tube.

16. The surgical instrument according to claim 15, wherein
the heat-shrinkable tube tightens the cleaning tube in a state where the heat-shrinkable tube is harder than the cleaning tube due to heat shrinkage.

17. The surgical instrument according to claim 15, wherein
a length of the heat-shrinkable tube in the cleaning liquid supply direction is equal to or greater than an outer diameter of the cleaning tube.

18. The surgical instrument according to claim 11, wherein
the cleaning tube is press-fitted into and attached to the first cleaning liquid supply hole.

19. The surgical instrument according to claim 11, wherein
the movement restriction portion is in contact with a peripheral edge portion of an opening of the first cleaning liquid supply hole on a downstream side.

20. A surgical instrument comprising:
a shaft;
an end effector provided on a side of one end of the shaft;
a housing including: a base provided on a side of the other end of the shaft and including an attachment surface at which the base is to be attached to a robot arm; a lid portion covering the base; and cleaning liquid supply holes to supply a cleaning liquid; and
a cleaning tube to supply the cleaning liquid to an inside of the shaft, wherein
the cleaning liquid supply holes comprise: a first cleaning liquid supply hole to which the cleaning tube is attached; a second cleaning liquid supply hole communicating with an inside of the housing; and a third cleaning liquid supply hole opening in a direction substantially orthogonal to an opening direction of the second cleaning liquid supply hole and communicating with the inside of the housing,
the lid portion is formed with the first cleaning liquid supply hole to which the cleaning tube is attached in such a manner that the first cleaning liquid supply hole communicates with the cleaning tube,
an outer circumferential surface of the cleaning tube is formed with a movement restriction portion that restricts a movement of the cleaning tube in a direction opposite to a direction of supplying the cleaning liquid in the cleaning tube,
the first cleaning liquid supply hole includes: a large diameter portion to which an end portion of a cleaning device for supplying the cleaning liquid is to be inserted; and a small diameter portion provided on a downstream side, in the cleaning liquid supply direction, of the large diameter portion,
the lid portion includes a projected portion protruded from an inner circumferential surface of the large diameter portion toward a center of the first cleaning liquid supply hole and forming the small diameter portion,
the cleaning tube includes a flange portion outwardly protruding therefrom in a radial direction of the cleaning tube, and
the movement restriction portion and the flange portion are arranged so as to sandwich the projected portion of the lid portion in the cleaning liquid supply direction.

* * * * *